(12) United States Patent
Cohen

(10) Patent No.: US 9,295,756 B2
(45) Date of Patent: Mar. 29, 2016

(54) METHODS FOR INDUCING IMMUNE TOLERANCE TO ORGAN TRANSPLANTS

(71) Applicant: NAYACURE THERAPEUTICS LTD., Haifa (IL)

(72) Inventor: Shahar Cohen, Kiryat Bialik (IL)

(73) Assignee: NAYACURE THERAPEUTICS LTD., Haifa (IL)

( * ) Notice: Subject to any disclaimer, the term of this patent is extended or adjusted under 35 U.S.C. 154(b) by 0 days.

(21) Appl. No.: 14/376,176

(22) PCT Filed: Jan. 31, 2013

(86) PCT No.: PCT/IL2013/050095
§ 371 (c)(1),
(2) Date: Aug. 1, 2014

(87) PCT Pub. No.: WO2013/114372
PCT Pub. Date: Aug. 8, 2013

(65) Prior Publication Data
US 2015/0030569 A1 Jan. 29, 2015

Related U.S. Application Data

(60) Provisional application No. 61/593,798, filed on Feb. 1, 2012.

(51) Int. Cl.
*A01N 1/02* (2006.01)
*A61L 27/36* (2006.01)

(52) U.S. Cl.
CPC ............. *A61L 27/3604* (2013.01); *A01N 1/021* (2013.01); *A01N 1/0226* (2013.01)

(58) Field of Classification Search
None
See application file for complete search history.

(56) References Cited

U.S. PATENT DOCUMENTS

| | | | |
|---|---|---|---|
| 4,673,649 A | 6/1987 | Boyce et al. | |
| 4,798,824 A | 1/1989 | Belzer et al. | |
| 4,879,283 A | 11/1989 | Belzer et al. | |
| 4,940,666 A | 7/1990 | Boyce et al. | |
| 5,643,712 A * | 7/1997 | Brasile | 435/1.2 |
| 5,702,881 A * | 12/1997 | Brasile et al. | 435/1.2 |
| 5,843,780 A | 12/1998 | Thomson | |
| 7,658,706 B2 * | 2/2010 | Squillace | 600/36 |
| 2002/0064768 A1 | 5/2002 | Polyak et al. | |
| 2013/0109088 A1 * | 5/2013 | Ott et al. | 435/350 |

FOREIGN PATENT DOCUMENTS

| | | |
|---|---|---|
| WO | 9531944 A1 | 11/1995 |
| WO | WO 95/31944 * | 11/1995 |
| WO | 0149210 A1 | 7/2001 |
| WO | 02014480 A2 | 2/2002 |
| WO | 2005038015 A1 | 4/2005 |
| WO | 2005099588 A2 | 10/2005 |
| WO | 2006077592 A2 | 7/2006 |
| WO | 2007025215 A2 | 3/2007 |
| WO | 2007025233 A1 | 3/2007 |
| WO | 2007124044 A2 | 11/2007 |
| WO | 2010091188 A1 | 8/2010 |
| WO | 2010120539 A2 | 10/2010 |
| WO | 2011002926 A2 | 1/2011 |
| WO | 2012005760 A1 | 1/2012 |

OTHER PUBLICATIONS

Daniel et al. "Development of the Human Umbilical Vein Scaffold for Cardiovascular Tissue Engineering Applicants" ASAIO J. 51(3):252-261(May-Jun. 2005).
Zhang H, et al "Shorter Hepatic Transit Time Can Suggest Coming Metastases" Ultrasound Med.; 29(5):719-26 (May 2010).
Zavorsky, et al "Red cell pulmonary transit times through the healthy human lung"Exp Physiol.; 88(2):191-200 (Mar. 2003).
Neishi Y, et al "Evaluation of bioavailability of nitric oxide in coronary circulation by direct measurement of plasma nitric oxide concentration" Proc Natl Acad Sci U S A.; 102(32):11456-61. Epub Jul. 28, 2005 (Aug. 2005).
McAllister et al., "Effectiveness of haemodialysis access with an autologous tissue-engineered vascular graft: a multicentre cohort study" Lancet 373, 1440-1446 (2009).
Deutsch et al., "Long-term experience in autologous in vitro endothelialization of infrainguinal ePTFE grafts" J Vasc Surg 49, 352-362 (2009).
Arts et al.,"A novel method for isolating pure microvascular endothelial cell from subcutaneous fat tissue ideal for direct cell seeding" Lab Invest 81, 1461-1465 (2001).
Kalka et al., "Transplantation of ex vivo expanded endothelial progenitor cells for therapeutic neovascularization" Proc Nat Acad Sci 97, 3422-3427 (2000).
Hill et al., "Ciruclation Endothelial Progenitor Cells, Vascular Function, and Cardiovascular Risk" New Eng J Med 348, 593-600 (2003).
Wigler et al. "DNA-mediated transfer of the adenine phosphoribosyltransferase locus into mammalian cells" Proc. Natl. Acad. Sci. USA 76:1373-1376 (1979).
Planat-Benard et al. "Spontaneous Cardiomyocyte Differentiation From Adipose Tissue Stroma Cells" Circ. Res. 94:223 (2004).
Silva et al. "The profile of gene expression of human marrow mesenchymal stem cells" Stem Cells 21:661 (2003).
Dekel B. et al. "Acute cellular rejection of human renal tissue by adoptive transfer of allogeneic human peripheral blood mononuclear cells into chimeric rats: sequential gene expression of cytokines, chemokines and cytolytic effector molecules, and their regulation by CTLA-4-Ig" hit Immunol. 11,1673 ( 1999).

(Continued)

*Primary Examiner* — Ralph Gitomer
(74) *Attorney, Agent, or Firm* — Browdy and Neimark, PLLC

(57) ABSTRACT

The present invention is directed to methods of treating an organ or a tissue prior to transplantation thereof into a recipient, comprising ablating the cells composing the blood vessels of said organ or tissue, preferably the cells lining the lumen surface of the blood vessels, thereby obtaining a treated viable organ or tissue having reduced immunogenicity. The invention is also directed to treated viable organs or tissues having reduced immunogenicity and uses thereof.

15 Claims, 5 Drawing Sheets

(56) References Cited

OTHER PUBLICATIONS

Higgins RM. Prevention of hyperacute rejection by removal of antibodies to HLA immediately before renal transplantation: et al. Lancet 348, 1208 (1996).

Suthanthiran et al. "Renal Transplantation" New Engl. J. Med. 331, 365 (1996.).

Midthum DE. et al, . "Medical Management and Complications in the Lung Transplant Recipient" Mayo Clin Proc. 72, 175 (1997).

Morrison VA. et al, "Clinical Characteristics of Post-Transplant Lymphoproliferative Disorder" Am J Med. 97, 14 (1994).

Senderowicz AM. et al, "Complete Sustained Response of a Refractory, Post-Transplantation, Large B-Cell Lymphoma to an Anti-CD22 Immunotoxin" Ann Intern Med. 126, 882 (1997).

Vincenti F. et al, "Interleukin-2-Receptor Blockade With Daclizumab to Prevent Acute Rejection in Renal Transplantation" New Engl. J. Med. 338, 161 (1998.).

Dantal J. et al. "Effect of long-term immunosuppression in kidney-graft receipients on cancer incidence: randomised comparison of two cyclosporin refimens" Lancet 351, 623 (1998.).

Hu et at., "Large scale mammalian cell culture" Curr. Opin. Biotechnol. 8:148, (1997).

S[Oer "Large Scale Mammalian Cell Culture: methods, applications and products" Curr. Opin. Biotechnol. 2:375, (1991).

Taflin et al "Immunological function of the endothelical cell within the setting of organ transplantation" Immunology Letters. 139 : 1-6 (2011).

* cited by examiner

Figure 2A
Figure 2B
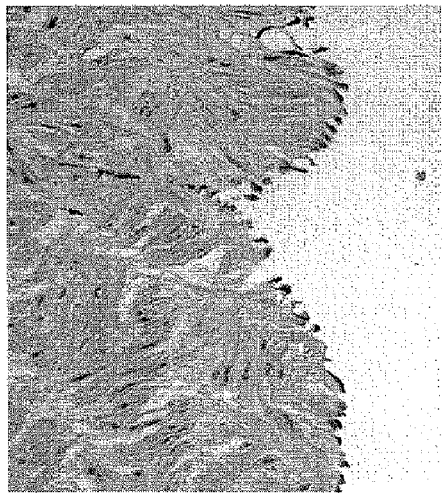
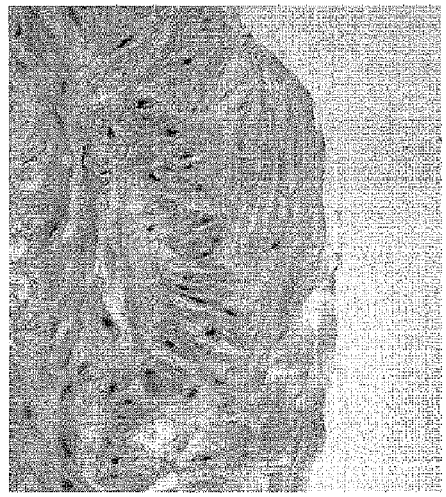

METHODS FOR INDUCING IMMUNE TOLERANCE TO ORGAN TRANSPLANTS

TECHNOLOGICAL FIELD

This invention relates generally to organ or tissue transplantation. In particular the invention concerns methods for rendering an organ or a tissue non immunogenic.

PRIOR ART

References considered to be relevant as background to the presently disclosed subject matter are listed below:
WO1995/31944
WO2001/049210
WO2010/120539
WO2012/005760
WO2001049210
WO2010120539
WO2012005760
WO2005038015
WO2006077592
Daniel et al. ASAIO J. 2005 May-June; 51(3):252-61

Acknowledgement of the above references herein is not to be inferred as meaning that these are in any way relevant to the patentability of the presently disclosed subject matter.

BACKGROUND

Organ or tissue transplantation is an effective treatment of many conditions associated with organ failure. The transplantation of donor's organ or tissue must be accompanied by chronic, systemic suppression of the recipient's immune system in order to avoid graft rejection.

The graft endothelial cells are known to play a critical role as initiators, participants and targets of both acute cellular rejection and antibody-mediated allograft rejection.

It is also known that transplantation of avascular embryonic tissues to replace the function of diseased organs offers several advantages relative to transplantation of fully differentiated adult organs: such avascular tissues are less immunogenic, and are less susceptible to humoral rejection than are adult organs (e.g. see WO2006077592).

Blood vessels of various species that were subjected to treatment destroying their entire cellular components but leaving intact the extracellular matrix (decellularization) and that were repopulated with cells have been investigated for their utility as scaffolds for vascular tissue engineering. Decellularized human umbilical veins (HUVs) have been suggested as scaffolds for vascular tissue engineering (Daniel et al.), whereas WO95/31944 discloses a method for treating grafts and rendering them nonthrombogenic and substantially non immunogenic by coating their inner lining with extracellular matrix (ECM).

General Description

In one aspect, the present invention provides a method of treating an organ or a tissue prior to transplantation thereof into a recipient, comprising:
(a) providing an organ or a tissue intended for transplantation; and
(b) Ablating the cells composing the blood vessels of said organ or tissue;
thereby obtaining a treated viable organ or tissue having reduced immunogenicity.

In one embodiment, step (b) comprises ablating the cells of the tunica intima cell layer lining the lumenal surface of the blood vessels of said organ or tissue.

In another embodiment, step (b) comprises ablating the cells composing the tunica intima cell layer and the tunica media cell layer of the blood vessels of said organ or tissue.

In another embodiment, step (b) comprises ablating the cells composing the tunica intima cell layer, the tunica media cell layer and the tunica adventitia cell layer of the blood vessels of said organ or tissue.

In certain embodiments, the step of ablating the cells comprises subjecting said organ or transplant to at least one cycle of perfusion with an ablating substance solution comprising at least one substance capable of destroying or neutralizing said cells.

In certain embodiments, the at least one substance is selected from a group consisting of a solubilizing agent, a detergent, a chelating agent, an enzyme, an antibody, a hypertonic solution, a hypotonic solution, a dehydrating agent, and any combination thereof.

In a specific embodiment, the detergent comprises at least one of SDS, CHAPS and TritonX.

In other embodiments, the substance is provided in a concentration sufficient to reduce the immunogenicity of the organ or tissue, as determined by the ablation of cells lining the lumenal surface of the blood vessels of the said organ or tissue.

In one embodiment, the perfusion is performed at a hypothermic temperature.

In one embodiment, the perfusion is performed for duration of about the transit time of said organ or tissue.

In one embodiment, the perfusion is performed for a duration which is smaller than the transit time of said organ or tissue.

In one embodiment, the perfusion is performed for a duration which is half the transit time of said organ or tissue.

In one embodiment, the perfusion is performed for a duration which is longer than the transit time of said organ or tissue.

In one embodiment, the perfusion is performed for duration of about 1 second to about 5 minutes.

In certain embodiments, the organ or the tissue is a mammalian organ or tissue.

In specific embodiments, the organ or the tissue are selected from the group consisting of primate, swine, cattle, sheep, rabbit, rodent and human organ or tissue.

In other specific embodiments the organ or the tissue are selected from the group consisting of a heart, lung, kidney, liver, pancreas, skin, uterus, bone, cartilage, small or large bowel, bladder, brain, breast, blood vessels, esophagus, fallopian tube, gallbladder, ovaries, pancreas, prostate, placenta, spinal cord, limb including upper and lower, spleen, stomach, testes, thymus, thyroid, trachea, ureter, urethra, uterus, vascular tissue, skin tissue, hepatic tissue, pancreatic tissue, neural tissue, urogenital tissue, gastrointestinal tissue, skeletal tissue including bone and cartilage, adipose tissue, connective tissue including tendons and ligaments, amniotic tissue, chorionic tissue, dura, pericardia, muscle tissue, glandular tissue, facial tissue and ophthalmic tissue.

In certain embodiments the method of the invention further comprises perfusing said organ or transplant with a preservation solution prior to, and/or after subjecting the organ or transplant to the at least one cycle of perfusion with the ablating substance solution.

In certain embodiments the method of the invention further comprises perfusing said organ or transplant with a protective solution during and/or after subjecting the organ or transplant to the at least one cycle of perfusion with the ablating substance solution.

In certain embodiments the method of the invention further comprises perfusing said organ or transplant with a washing solution prior to, after, and/or in between the perfusion cycles.

In one embodiment the method of the invention is performed ex vivo.

In certain embodiments, the blood vessels of the organ or tissue are perfused in a retrograde fashion, in an antegrade fashion or in a combination of retrograde and antegrade fashions.

In certain embodiments the method of the invention further comprises contacting said treated viable organ or tissue with a population of cells under conditions in which said cells engraft, multiply and/or differentiate on the lumenal surface of the blood vessels of the treated viable organ or tissue.

In one embodiment, the cells are injected into said treated viable organ or tissue.

In another embodiment, the cells are perfused into said treated viable organ or tissue.

In certain embodiments, the cells are autologous cells.

In another aspect, the present invention provides an isolated viable organ or tissue having reduced immunogenicity, wherein cells lining the lumenal surfaces of its vasculature are ablated, and wherein the remaining cell layers in the organ or tissue are intact and viable.

In certain embodiments, the isolated viable organ or tissue having reduced immunogenicity is obtainable by the methods of the invention. In one embodiment, the isolated viable organ or tissue having reduced immunogenicity is obtained by the methods of the invention.

In certain embodiments, the present invention provides an isolated viable organ or tissue having reduced immunogenicity for use in transplantation.

In yet another aspect, the present invention provides a method of treating a patient in need of transplantation, comprising:
 (a) obtaining the treated viable organ or tissue of the invention; and
 (b) transplanting said treated viable organ or tissue into the patient.

In yet another aspect, the present invention provides a method of evaluating the suitability of a tissue or organ for transplantation comprising:
 (a) treating the tissue or organ to ablate the cells composing the blood vessels of the tissue or organ according to the methods of the invention;
 (b) testing the efficacy of cell removal; and
 (c) validating the viability of the remaining, non-ablated cells of the tissue or organ.

In one embodiment, the testing in step (b) is performed by histology and/or immunohistochemistry analysis.

In yet another aspect, the present invention provides a method of evaluating the suitability of a tissue or organ for transplantation comprising:
 (a) treating the tissue or organ to ablate the cells composing the blood vessels of the tissue or organ according to the method of the invention,
 (b) transplanting said tissue or organ into a recipient, and
 (c) testing the tolerance of the recipient to the transplanted organ or tissue.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 2 is a X100 magnification photomicrograph of H&E-stained histological analysis of cross sections of native (A) and treated (B) blood vessels: pre-treated vessel (b) is devoid of the first layer of cells lining the luminal surface, while the subendothlial layer remains intact, and deeper layers of the vessel wall remain viable and intact.

DETAILED DESCRIPTION OF EMBODIMENTS

Figure 1A:
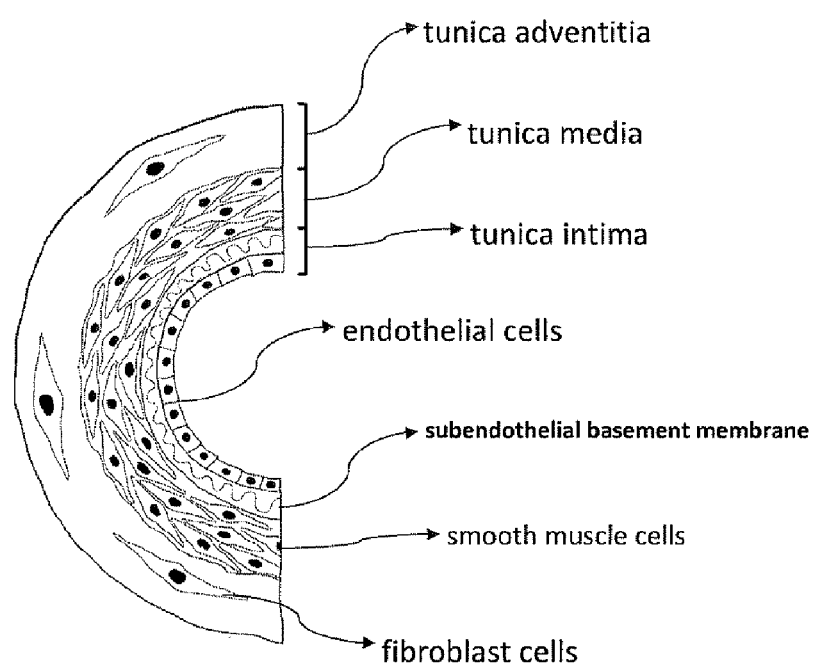
FIG. 1 is a schematic representation of a blood vessel before (A) and after (B) being treated in accordance with the invention.

Unless defined otherwise, all technical and scientific terms used herein generally have the same meaning as commonly understood by one of ordinary skill in the art to which this invention belongs.

The instant invention is most clearly understood with reference to the following definitions:

As used in the specification and claims, the singular form "a," "an," and "the" include plural references unless the context clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

As used herein, a "graft" refers to a tissue or organ that is implanted into an individual, typically to replace, correct or otherwise overcome a defect. The tissue or organ may consist of cells that originate from the same individual; this graft is referred to herein by the following interchangeable terms: "autograft", "autologous transplant", "autologous implant" and "autologous graft". A graft from a genetically different individual of the same species is referred to herein by the following interchangeable terms: "allograft", "allogeneic transplant", "allogeneic implant" and "allogeneic graft". A graft from an individual to his identical twin is referred to herein as an "isograft", a "syngeneic transplant", a "syngeneic implant" or a "syngeneic graft". A "xenograft", "xenogeneic transplant" or "xenogeneic implant" refers to a graft from one individual to another of a different species.

As used herein the term "organ" refers to a solid vascularized organ that performs a specific function or group of functions within an organism. The term organ includes, but is not limited to heart, lung, kidney, liver, pancreas, skin, uterus, bone, cartilage, small or large bowel, bladder, brain, breast, blood vessels, esophagus, fallopian tube, gallbladder, ovaries, pancreas, prostate, placenta, spinal cord, limb including upper and lower, spleen, stomach, testes, thymus, thyroid, trachea, ureter, urethra, uterus.

The term "tissue" as used herein refers to any type of tissue in human or animals, and includes, but is not limited to, vascular tissue, skin tissue, hepatic tissue, pancreatic tissue, neural tissue, urogenital tissue, gastrointestinal tissue, skeletal tissue including bone and cartilage, adipose tissue, connective tissue including tendons and ligaments, amniotic tissue, chorionic tissue, dura, pericardia, muscle tissue, glandular tissue, facial tissue, ophthalmic tissue.

As used herein the term "treated" or "pre-treated" viable organ or tissue" refers to an organ or tissue that was treated in accordance with the invention by ablating the cells composing the blood vessels of said organ or tissue while keeping the remaining cell layers in the organ or the tissue intact and viable. Preferably, a "treated viable organ or tissue" is an organ or tissue that was treated in accordance with the invention by ablating the cells lining the lumenal surfaces of the vasculature in the organ or the tissue. The treated viable organ or tissue obtained by the methods of the invention is not a decellularized organ or tissue. The term "decellularized" shall be understood to mean an organ from which substantially all of the cells have been removed. A decellularization process eliminates substantially all the cells and maintains only the extracellular matrix of the organ.

As used herein, the term "cells composing the blood vessels" refers to the cells composing the three layers of the blood vessel wall, i.e. the tunica intima, which is composed of a single layer of endothelial cells and sub-endothelial basement membrane; the tunica media, which is composed of smooth muscle cells and elastic fibers; and the tunica adventitia, which is composed of connective tissue cells, collagen, and elastic fibers.

As used herein the term "cells lining the lumenal surfaces of the vasculature" refers to the cells of the tunica intima.

An "extracellular matrix" ("ECM") shall be understood to be the non cellular portion of an organ that provides structural support for the cells. ECM refers to one or more substances that line the extracellular space around cells in vivo or in culture and support cell growth. Such substances are derived from a cell that is or was present within a tissue but is not contained within the plasma membrane of a cell. Examples of ECM components include collagen, elastin, proteoglycans, fibronectin, and laminin.

"Vasculature" or "vascular" are terms referring to the system of vessels carrying blood (as well as lymph fluids) throughout the body, and within organs and tissues.

"Blood vessel" refers to any of the vessels of the mammalian vascular system, including arteries, arterioles, capillaries, venules, veins, sinuses, and vasa vasorum. The wall of a blood vessel consists typically of an outer layer (adventitia) separated by an external elastic lamina from a middle layer (media) which is separated by an internal elastic lamina from an inner layer (intima). The adventitia is a layer of loose connective tissue which generally includes a network of microvessels (vasa vasorum), fibroblasts, and immune cells such as lymphocytes and macrophages. The media comprises circular layers of smooth muscle cells and elastic fibers. The intima is made up of a monolayer of endothelial cells and sub-endothelial basement membrane.

"Microvessel" "microvascular" or "microvasculature" as used herein, are terms referring to the arterioles, capillaries, venules, and adventitial microvessels. Microvessels generally comprise endothelial cells surrounded by one or a few layers of smooth muscle cells. Arteriole refers to a minute arterial branch, especially one just proximal to a capillary. Capillary refers to any one of the minute vessels that connect the arterioles and venules, forming a network in virtually all organs and tissues. Venules refer to any of the small vessels that collect blood from the capillary plexuses and join to form veins.

"Adventitial microvessel" refers to microvessels that supply blood to the adventitia of larger blood vessels such as arteries. The network of these adventitial microvessels is commonly referred to as the vasa vasorum. Adventitial microvessels are believed to be supplied with blood from the lumen of the parent vessel (e.g., the artery) via small microvessels traversing the vessel intima and media.

"Microvascular cell" refers to cells that make up the structure of microvessels.

"Endothelium" refers to the layer of "endothelial cells" that generally lines the luminal surface of the heart and blood vessels, as well as vessels of the lymphatic system.

A "preservation solution" shall be understood to be any fluid capable of improving or maintaining the vitality of a cell, tissue and organ (including tissues and organs that were treated to ablate the cells lining the lumen surfaces of their vasculature and such treated organs and tissues that were repopulated with cells) Improving or maintaining vitality can include one or more of the following: maintenance of appropriate osmotic pressure, maintenance of appropriate temperature, inhibition of decay, inhibition of microbial growth, and the like.

As used herein the term "ablating substance solution" or "substance solution" refers to any fluid comprising an effective amount of at least one substance capable of destroying, eliminating or neutralizing the cells composing the blood vessels of the vasculature in the organ or tissue. Preferably, destroying, eliminating or neutralizing the cells lining the lumenal surfaces of the vasculature in the organ or tissue. An effective amount means an amount appropriate for achieving the effect within the context of the intended use. In this particular case "an effective amount" refers to a concentration sufficient to reduce the immunogenicity of the organ or tissue, as determined by the absence of immunogenic cells lining the luminal surface of the vessels, as can be analyzed for example by histology. For example, immunogenicity of the organ or tissue can be characterized in vitro by staining for Major histocompatibility complex (MHC) Class I and II antigens.

As used herein, the term "ablating agent" or "ablating substance" refers to an agent or a substance capable of destroying, eliminating or neutralizing the cells composing the blood vessels of the vasculature in the organ or tissue. Preferably, destroying, eliminating or neutralizing the cells lining the lumenal surfaces of the vasculature in the organ or tissue. The ablating substance may be, but is not limited to a detergent (e.g. SDS, CHAPS, or Triton X), a chelating agent (e.g. EDTA), an enzyme (e.g. trypsin, collagenase) or an antibody.

The term ablating substance solution also encompasses a hypertonic solution (e.g. 3M NaCl) or a hypotonic solution (e.g. distilled water).

As used herein the term "washing solution" refers to any physiological solution, e.g. 0.9% saline.

As used herein the term "protective solution" refers to any fluid designed to protect the ablated blood vessels from undesired injuries (related for example to inflammation, proteolysis, oxidation, infection, thrombosis). The protective solution comprises one or more of the following compounds: antioxidants, anti-inflammatory agents, anti-microbial agents, anti-thrombotic agents, protease inhibitors, ECM molecules, and sera or sera-derived factions, wherein the sera are derived from the intended recipient.

"Hypothermic" shall be understood to mean temperatures below 37 degrees centigrade, and preferably below 35 degrees centigrade, or significantly lower than 37 degrees centigrade. For example, "hypothermic" temperatures include, but are not limited to, temperatures between about 0 degrees centigrade to about 15 degrees C., temperatures between about 1 degrees centigrade to about 8 degrees C., temperatures between about 3 degrees centigrade to about 5 degrees C., and the like.

"Normothermic" shall be understood to mean temperatures above room temperature. For example, "normothermic" temperatures include, but are not limited to, temperatures between about 25 degrees centigrade and about 42 degrees C., temperatures between about 30 degrees centigrade and about 38 degrees C., temperatures between about 37 degrees centigrade and about 37.5 degrees C., and the like.

"Room temperature" shall be understood to mean a temperature between about 15 degrees centigrade and about 25 degrees centigrade. For example, "room temperature" includes, but is not limited to, temperatures between about 18 degrees centigrade and about 23 degrees C., temperature between about 19 degrees centigrade and about 21 degrees C., temperatures between about 24 degrees centigrade and about 25 degrees C., temperatures between about 20 degrees centigrade and about 21 degrees C., and the like.

As used herein "mammal" includes embryonic, juvenile, and adult mammals, unless the context clearly indicates otherwise. Mammals include, for example, humans, cows, sheep, big-horn sheep, goats, buffalos, antelopes, oxen, horses, donkeys, mule, deer, elk, caribou, water buffalo, camels, llama, alpaca, rabbits, pigs, mice, rats, guinea pigs, hamsters, dogs, cats, and primates such as monkeys.

A "donor" shall be understood to include any mammal including, but not limited to, humans, primates, swine, cattle, sheep, horses, cats, dogs, rabbits and rodents, from which an organ or tissue are obtained.

A "recipient" shall be understood to include any compatible transplant host. By "compatible" is meant a host that will accept the donated graft. Examples of potentially useful recipients include animals, preferably mammals such as farm animals, for example, horses, cows or sheep; household pets, for example, dogs or cats; laboratory animals, such as mice, rats, gerbils or guinea pigs; or primates, for example, apes or human beings. Most preferably, the recipient is a human being. If both the donor of the graft and the host are human, they are preferably matched for HLA class II antigens to as to improve histocompatibility.

The term "repopulation" shall be understood to be any process for engrafting one or more cells within an organ or tissue that was treated to ablate the cells composing its blood vessels, or preferably, treated to ablate the cells lining its lumenal surfaces, namely, a process for repopulating the lumenal surfaces of the vasculature of such treated organs or tissues, with, for example autologous endothelial cells.

As used herein "endogenous" refers to any material from or produced inside an organism, cell or system.

"Exogenous" refers to any material introduced into or produced outside an organism, cell, or system.

"Proliferation" is used herein to refer to the reproduction or multiplication of similar forms, especially of cells. That is, proliferation encompasses production of a greater number of cells, and can be measured by, among other things, counting the number of cells, measuring incorporation of —H-thymidine into the cell, and the like.

"Differentiation medium" is used herein to refer to a cell growth medium comprising an additive or a lack of an additive such that a stem cell, a progenitor cell or other such cell, that is not fully differentiated, develops into a cell with some or all of the characteristics of a differentiated cell when incubated in the medium.

"Growth factor" refers to a substance that is effective to promote the growth of cells. For example, basic fibroblast growth factor (bFGF), acidic fibroblast growth factor (aFGF), epidermal growth factor (EGF)$_5$ insulin-like growth factor I (IGF-I), insulin-like growth factor-II (IGF-II), platelet-derived growth factor (PDGF), vascular endothelial growth factor (VEGF), bone morphogenic proteins (BMPs), insulin, cytokines, chemokines, morphogens.

The term "attached" as used herein encompasses interaction including, but not limited to, covalent bonding, ionic bonding, and mechanical interactions.

As used herein, a "stem cell" is a cell with the developmental potential to produce a more specialized cell type and at the same time to replicate itself. A stem cell may divide to produce two daughters that are themselves stem cells or it may divide to produce a daughter that is a stem cell and a daughter that is a more specialized cell type. A stem cell may originate from the embryo, fetus, or adult.

A "progenitor cell" or "precursor cell" is a cell which occurs in fetal or adult tissues and is partially specialized. It divides and gives rise to differentiated cells.

As used herein, a "pluripotent stem cell" or "induced pluripotent stem cell" is a stem cell with the developmental potential to produce ectodermal cell types, mesodermal cell types, and endodermal cell types. An "embryonic stem cell" is a type of totipotent stem cell. That is, it is a cell that can give rise to every cell type in a mammal. A totipotent stem cell is a type of "pluripotent stem cell".

A "differentiated cell" is any cell with less developmental potential than a pluripotent stem cell.

As used herein, a "lineage-restricted stem cell" is a stem cell that can only give rise to cell types within one germ layer (i.e., to cell types within ectoderm or mesoderm or endoderm lineages). The lineage-restricted stem cell may have the potential to give rise to all cell types within the germ layer or it may only have the potential to give rise to a subset of cell types within the germ layer.

As used herein, a "pluripotent stem cell marker" is an mRNA or protein that is present in a pluripotent stem cell but absent in a lineage-restricted stem cell.

A "somatic stem cell" is a stem cell found in or isolated from a differentiated tissue, which can renew itself and give rise to at least one specialized cell type of the germ layer from which it originated. Non-limiting examples of somatic stem cells include "hematopoietic stem cells", "bone marrow stromal stem cells", "neural stem cells", "epithelial stem cells", and "skin stem cells". "Hematopoietic stem cells" give rise to all the types of blood cells: red blood cells, B lymphocytes, T lymphocytes, natural killer cells, neutrophils, basophils, eosinophils, monocytes, macrophages, and platelets. "Bone marrow stromal stem cells" give rise to a variety of cell types: bone cells (osteocytes), cartilage cells (chondrocytes), fat cells (adipocytes), and other kinds of connective tissue cells such as those in tendons. "Neural stem cells" in the brain give rise to its three major cell types: nerve cells (neurons) and two categories of non-neuronal cells—astrocytes and oligodendrocytes. "Epithelial stem cells" in the lining of the digestive tract occur in deep crypts and give rise to several cell types: absorptive cells, goblet cells, Paneth cells, and enteroendocrine cells. "Skin stem cells" occur in the basal layer of the epidermis and at the base of hair follicles. The epidermal stem cells give rise to keratinocytes, which migrate to the surface of the skin and form a protective layer. The follicular stem cells can give rise to both the hair follicle and to the epidermis.

A "somatic cell" is defined herein as a diploid cell of any tissue type that does not contribute to the propagation of the genome beyond the current generation of the organism. All cells except for germ cells are somatic cells and constitute the individual's body.

The terms "cell culture" and "culture" encompass the maintenance of cells in an artificial, in vitro environment. It is to be understood, however, that the term "cell culture" is a generic term and may be used to encompass the cultivation not only of individual cells, but also of tissues, organs, organ systems or whole organisms, for which the term "tissue culture" may occasionally be used interchangeably with the term "cell culture."

The terms "cell culture medium" or "culture medium" (plural "media" in each case) refer to a nutritive solution for cultivating cells and may be used interchangeably.

As used herein, "scaffold" refers to a structure, comprising a biocompatible material that provides a surface suitable for adherence and proliferation of cells. A scaffold may further provide mechanical stability and support. A scaffold may be in a particular shape or form so as to influence or delimit a three-dimensional shape or form assumed by a population of proliferating cells.

As used here, "biocompatible" refers to any material, which, when implanted in a mammal, does not provoke an adverse response in the mammal.

"Tissue engineering" refers to the process of generating tissues ex vivo for use in tissue replacement or reconstruction. Tissue engineering is an example of "regenerative medicine" which encompasses approaches to the repair or replacement of tissues and organs by incorporation of cells, genes or other biological building blocks, along with bioengineered materials and technologies.

As used herein, to "alleviate" a disease, defect, disorder or condition means reducing the severity of one or more symptoms of the disease, defect, disorder or condition.

As used herein, the terms "treat", "treating" or "treatment" refers to the administration of therapy to an individual in an attempt to reduce the frequency and/or severity of symptoms of a disease, defect, disorder, or adverse condition of a patient.

As used herein, the terms "prevent", "preventing" and "prevention" refer to the administration of therapy to an individual who may ultimately manifest at least one symptom of a disease, disorder, or condition, but who has not yet done so, to reduce the chance that the individual will develop the symptom of the disease, disorder, or condition over a given period of time. Such a reduction may be reflected, for example, in a delayed onset of the at least one symptom of the disease, disorder, or condition in the patient.

The term "transplant rejection" encompasses both acute and chronic transplant rejection. "Acute rejection" is the rejection by the immune system of a tissue transplant recipient when the transplanted tissue is immunologically foreign. Acute rejection is characterized by infiltration of the transplant tissue by immune cells of the recipient, which carry out their effector function and destroy the transplant tissue. The onset of acute rejection is rapid and generally occurs in humans within a few weeks after transplant surgery. Generally, acute rejection can be inhibited or suppressed with immunosuppressive drugs such as rapamycin, cyclosporin A, anti-CD40L monoclonal antibody and the like.

"Chronic transplant rejection" generally occurs in humans within several months to years after engraftment, even in the presence of successful immunosuppression of acute rejection. Fibrosis is a common factor in chronic rejection of all types of organ transplants.

In general, there are two types of blood vessels, arteries and veins. The walls of both arteries and veins are composed of three layers, or tunics. The inner layer is referred to as the tunica intima, which is composed of a single layer of endothelial cells and sub-endothelial basement membrane. The middle layer is referred to as the tunica media, and consists of smooth muscle cells and elastic fibers. The outer layer is referred to as the tunica adventitia, which is the outer covering of the vessel, and is composed of connective tissue cells, collagen, and elastic fibers. The tunica adventitia includes small vessels, referred to as vasa vasorum, which supply nutrients to the tissue. The connective tissue fibers of the tunica adventitia typically blend into those of adjacent tissues, stabilizing and anchoring the blood vessel.

FIG. 1 is a sectional view of a blood vessel that schematically illustrates the orientation of these layers.

Microvessels (which include arterioles, capillaries, venules, and the vasa vasorum) may differ from the general structural model outlined above in that the three layers in such small vessels may not be well defined. For instance, capillaries may comprise a monolayer of endothelial cells surrounded by a single layer of smooth muscle cells without any well-defined elastic layers.

The endothelial cells lining the blood vessels of transplanted organs are largely responsible for the initiation of alloimmune responses of the recipient against the graft, as these cells are responsible for presentation of alloantigens to circulating T cells of the recipient.

Accordingly, most allo-antibodies implicated in antibody-mediated rejection are directed against MHC antigens expressed by endothelial cells.

In addition, the endothelial cells are also responsible for induction of pro-inflammatory T cells under inflammatory conditions, and are also involved in induction of non-immune mechanisms, since injury to endothelial cells may lead to thrombosis.

Accordingly, the present invention relates to novel methods for inducing immune tolerance to tissue or organ transplants by removing, destroying or neutralizing (ablating) the cells composing the blood vessels, or preferably, the cells lining the lumenal surface of blood vessels of the transplanted tissue or organ (also referred to herein as the "graft"). The absence of these cells prevents or reduces the recipient's immune response to the foreign graft.

Figure 1B:
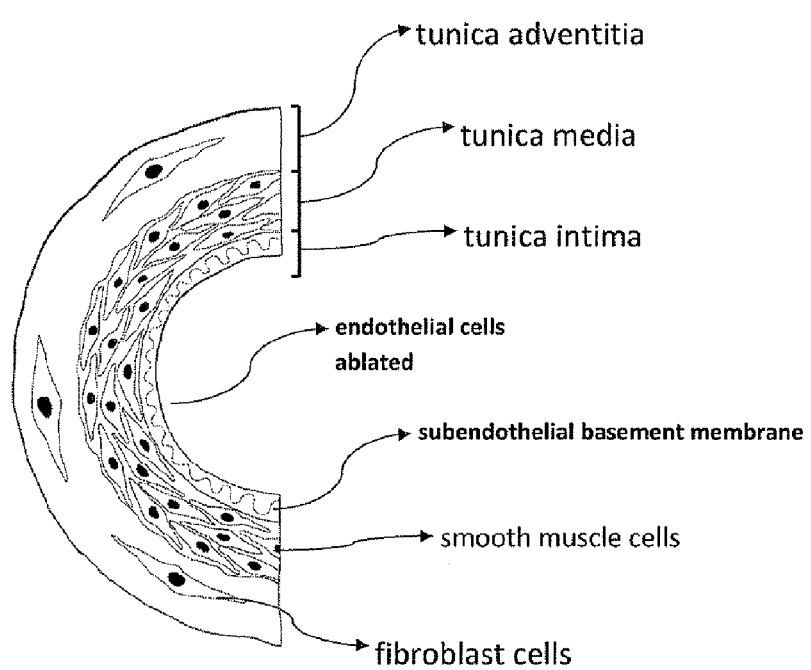
Figure 3A:
FIG. 3 is a X100 magnification photomicrograph of immunohistochemistry analysis of cross sections of native (A) and treated (B) blood vessels stained with anti-human CD34 antibody: treated vessel (B) is devoid of any CD34 positive cells.
Figure 3B:
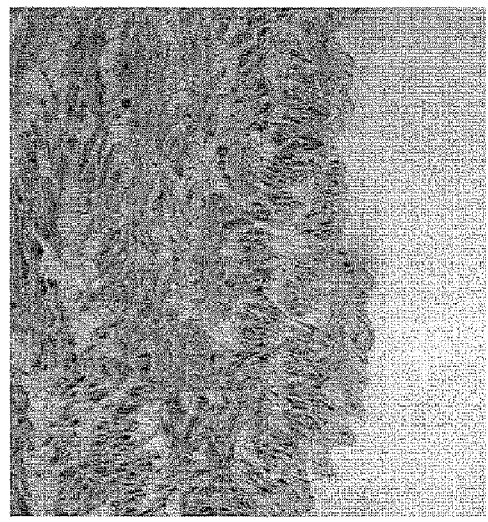

As can be seen in FIGS. 1, 2 and 3, the endothelial cells which form the inner lining of the blood vessel are selectively eliminated (FIGS. 1A, 2A and 3A) while leaving the remaining tissue and cell layers intact and viable FIGS. 1B, 2B and 3B). Thereby a graft lacking the endothelial cell layer is obtained and may be used for transplantation.

The present invention also relates to methods for inhibiting rejection, or for delaying the onset of rejection of a transplanted tissue or organ in a recipient mammal by removing or destroying the cells lining the luminal surface of blood vessels of the transplanted tissue or organ.

In another aspect, the present invention provides methods of treating a disorder comprising transplanting into a patient in need thereof a tissue or organ transplant, wherein said tissue or organ transplant were pre-treated by removing or destroying or neutralizing the cells lining the luminal surface of blood vessels of the transplanted tissue or organ.

In another aspect, the present invention provides an isolated tissue or an isolated organ for use as a transplant, wherein said isolated tissue or isolated organ were treated prior to transplantation by removing or destroying or neutralizing the cells lining the luminal surface of blood vessels of the isolated tissue or isolated organ.

In another aspect, the present invention provides a method of evaluating the suitability of a tissue or organ for transplantation comprising (a) pre-treating the tissue or organ to ablate the cells lining the luminal surface of the blood vessels of the tissue or organ, (b) testing the efficacy of cell removal, (c) validating the viability of the remaining, non-ablated cells of the tissue or organ.

In one embodiment, the testing and the evaluation are performed by histology and immunohistochemistry analysis.

In another aspect, the present invention provides a method of evaluating the suitability of a tissue or organ for transplantation comprising (a) pre-treating the tissue or organ to ablate the cells lining the luminal surface of the blood vessels of the tissue or organ, (b) transplantation of said tissue or organ, and (c) testing the tolerance of the recipient to the transplanted organ or tissue.

Accordingly, in one aspect the present invention provides a method of treating an organ or a tissue prior to transplantation thereof into a recipient, comprising:
 a. providing an organ or a tissue intended for transplantation; and
 b. Ablating the cells composing the blood vessels of said organ or tissue; thereby obtaining a treated viable organ or tissue having reduced immunogenicity.

In particular, the present invention provides a method of treating the cells lining the lumenal surfaces in the vasculature of said organ or tissue.

In certain embodiments, said method comprises removing the organ or tissue intended for transplantation from the donor.

In certain embodiments the organ or tissue are an organ or tissue suitable for perfusion. As used herein the term "organ or tissue suitable for perfusion" refers to a vascularized organ or tissue, wherein the vasculature of the organ or tissue comprises at least one blood vessel that can be associated with tubes and circuits in a perfusion system, such that a perfusion solution can be infused through the organ or tissue.

The term "transplantation" and variations thereof refers to the insertion of a graft into a recipient, whether the transplantation is syngeneic (where the donor and recipient are genetically identical), allogeneic (where the donor and recipient are of different genetic origins but of the same species), or xenogeneic (where the donor and recipient are from different species). Thus, in a typical scenario, the host is human and the graft is an isograft, derived from a human of the same or different genetic origins. In another scenario, the graft is derived from a species different from that into which it is transplanted, including animals from phylogenically widely separated species, for example, a baboon heart being transplanted into a human host.

The donor tissue or organ can be taken from any source, whether from cadavers or living donors. Examples of suitable donors include live animals such as laboratory animals, for example, dogs, cats, mice, rats, gerbils, guinea pigs, cows, primates, or human beings. Donors are preferably mammalian, including human beings.

Human donors are preferably voluntary, blood-related donors that are normal on physical examination and of the same major ABO blood group, because crossing major blood group barriers can prejudice the survival of an allograft. It is, however, possible to transplant, for example, a kidney of a type O donor into an A, B or AB recipient.

Preferably, the donor is of the same species as the recipient.

In certain embodiments the organ or tissue is selected from the group consisting of a heart, lung, kidney, liver, pancreas, skin, uterus, bone, cartilage, small or large bowel, bladder, brain, breast, blood vessels, esophagus, fallopian tube, gallbladder, ovaries, pancreas, prostate, placenta, spinal cord, limb including upper and lower, spleen, stomach, testes, thymus, thyroid, trachea, ureter, urethra, uterus, vascular tissue, skin tissue, hepatic tissue, pancreatic tissue, neural tissue, urogenital tissue, gastrointestinal tissue, skeletal tissue including bone and cartilage, adipose tissue, connective tissue including tendons and ligaments, amniotic tissue, chorionic tissue, dura, pericardia, muscle tissue, glandular tissue, facial tissue and ophthalmic tissue.

In one embodiment the donor of the organ or tissue is an animal.

In another embodiment the donor of the organ or tissue is a human.

The donor of the organ or tissue can be a living donor or a deceased donor, namely a cadaveric donor.

In one embodiment the organ or tissue are treated prior to harvesting from a deceased heart-beating donor.

In one embodiment the recipient of the organ or tissue is an animal.

In a preferred embodiment the recipient of the organ or tissue is a human.

As used herein the term "harvesting" refers to a surgical procedure in which an organ or a tissue is obtained from the donor.

In certain embodiments, said method further comprises perfusing the organ or tissue with a preservation solution after obtaining the organ or tissue from the donor.

The preservation solution may be but is not limited to University of Wisconsin (UW) solution, ViaSpan® (described e.g. in U.S. Pat. Nos. 4,798,824 and 4,879,283), Vasosol, (described e.g. in U.S. Patent Application publication 2002/0064768), other crystalloid solution, dextran, HES (hydroxyethyl starch), 0.9% saline solution supplemented with 40 Units/ml of heparin, or the like, as disclosed for example in U.S. Pat. No. 6,492,103. The organ can then be stored statically, at low temperatures (for example at a temperature of from about 1° C. to about 10° C.), until further processing. In one embodiment, the organ is kept at 4° C. The organ can be stored, for example, on ice.

It should be apparent to one of skill in the art that any potential protocol that prepares the organ or tissue for the pre-treatment could be used within the scope of the present invention.

The immune tolerance is achieved by selective ablation of the inner lining of the blood vessels of the organ or tissue, in a way that disrupts the bilayer cell membrane of the lining endothelial cells, or neutralizes the antigens found on the cell membrane of these cells or presented by them. Thereby, the viability of the donor endothelial cells lining the blood vessels which are present in the organ or tissue transplant is selectively reduced or eliminated, while the sub-endothelial vascular basement membrane and other extracellular matrix components remain intact. Cells found in deeper layers of the blood vessels as well as in deeper layers of the organ or the tissue remain intact and viable.

The selective ablation of the cells can be achieved at any desired depth of the walls of the blood vessels, including beyond the walls of the blood vessels Namely, in certain embodiments, at least 50%, 60%, 70%, 80%, 90%, 99% or 99.9% of the cells of the treated tissue or organ remain intact and viable.

In other embodiments, at most 49%, 40%, 30%, 20%, 10%, 1%. 0.1% of the cells of the treated tissue or organ are affected by the treatment of the invention.

In one embodiment, the cells that are eliminated are endothelial cells.

In certain embodiments the ablation of the endothelial cells of the blood vessels of the organ or tissue are performed by a mechanical or physical means. In a specific embodiment said mechanical means is agitation. In another specific embodiment said mechanical means is dehydration by passing a gas steam through the blood vessels.

In one embodiment, the step of ablating the cells comprises performing at least one cycle of perfusion of said organ or tissue with a solution (also termed "ablating solution") comprising at least one substance capable of destroying, eliminating or neutralizing said cells, in a concentration sufficient to reduce the immunogenicity of the organ or tissue, as determined by the absence of immunogenic endothelial cells lining the luminal surface of the vessels, as can be analyzed for example by histology.

Specifically, said at least one substance is capable of disrupting the integrity of the endothelial cells lining the organ or tissue blood vessels.

As used herein the term "perfusion" relates to a process of infusing or passaging a fluid through the vessels of an organ. In one embodiment, the perfusion is performed in an apparatus designed to perfuse an effective amount of a substance through the blood vessels of the organ/tissue and bring the substance into contact with the cells lining the lumenal surfaces of the vasculature of the organ or tissue, such that the cells are disrupted or neutralized but the remaining parts of the organ or tissue remain intact and viable. Preferably, the perfusion takes place prior to transplanting the organ or tissue into a recipient.

The perfused substance reacts with the cells lining the luminal surface of the tissue or organ and affects their viability or structure.

In certain embodiments the free ends of the artery and vein of the tissue or organ are cannulated and the tissue or organ is then subjected to perfusion.

In general the methods employ a variety of chemical, biochemical, and/or physical means to disrupt, degrade, neatralize and/or destroy cellular components and/or facilitate removal of the cells and cellular components. Such methods are disclosed, for example, in WO2011002926, WO2007025233, WO2010091188, and WO2002014480.

The present invention is not limited to these techniques but also includes modifications of these techniques, as well as other techniques currently available or developed in the future.

The effects of ablation on the graft structure may be evaluated by light microscopy, ultrastructural examination, etc, or by biochemical tests which are well known in the art.

Selection and interpretation of such tests will depend, in general, upon the nature of the organ or tissue and the purpose for which it is intended, in addition, the treatment preferably does not result in a cytotoxic environment that significantly inhibits subsequent steps such as re-population in vitro or population of the organ or tissue by cells of a recipient in vivo.

In one embodiment, the ablation solutions enhance cell lysis and destruction of cellular components, i.e. they contain agents that disrupt and/or degrade cellular constituents such as cell membranes, proteins, nucleic acids, etc. Therefore, they must be administered in a controlled manner so as to avoid undesired excessive cell ablation.

In another embodiment, the ablation solution comprises as the ablating substance a compound that does not disrupt the cells but rather neutralizes their immunogenicity, e.g. an antibody.

Ablation may be accomplished using a single ablating substance, or the tissue or organ may be perfused sequentially or simultaneously with two or more ablating substances.

In certain embodiments the perfused ablating substance is a solubilizing agent, a detergent, an emulsifying agent, or any combination thereof. Non limiting examples of suitable detergents include ionic detergents, e.g. SDS (sodium dodecyl sulfate), and nonionic detergents, e.g. Triton X (tert-octylphenylpolyoxyethylene), or a combination thereof.

In one embodiment, the ablating substance solution comprises one or more of Triton X, CHAPS (3-[(3-cholamidopropyl)-dimethyl-ammonio]-1-propanesulfonate), or SDS in phosphate buffered saline (PBS). Other suitable detergents include polyoxyethylene (20) sorbitan mono-oleate and polyoxyethylene (80) sorbitan mono-oleate (Tween 20 and 80), sodium deoxycholate, and octyl-glucoside.

The ablation of the endothelial cells may cause residual damage to the extracellular matrix and the subendothelial layers, due to proteases that are released upon lysis of the cells. Therefore, in certain embodiments of the invention various additives such as metal ion chelators, e.g., EDTA (ethylenediaminetetraacetic acid) and/or protease inhibitors are included in the ablation solution. Suitable protease inhibitors include, for example, one or more of phenylmethylsulfonyl-fluoride (PMSF), aprotinin, leupeptin, and N-ethylmaleimide (NEM).

The ablation solution may further include various enzymes that degrade cellular components. Such enzymes include nucleases (e.g., DNAses such as DNAse I, RNAses such as RNAse A), phospholipases (e.g., phospholipase A or C), and proteases (e.g. dispase II, trypsin, and thermolysin).

The activity of proteases is a function of time, temperature, and concentration, and these variables may be appropriately adjusted to achieve acceptable ablation without unacceptable destruction of the extracellular matrix and underlying non-endothelial cell layers. Nucleases are typically employed at a concentration of between 0.1 µg/ml and 50 µg/ml. Preferably, DNAse I is used at a concentration of about 10 µg/ml and RNAse A is used at a concentration of about 1.0 µg/ml for. The nucleases are preferably employed in a physiologically buffered solution at a temperature of between about 20° C. to 38° C., preferably 37° C.

The ablation solution typically includes a buffer. Suitable buffers include organic buffers such as Tris(hydroxymethyl) aminomethane (TRIS), (N-[2-hydroxyethyl]piperazine-N'-[2-ethanesulfonic acid] (HEPES), and the like. Buffers including sodium phosphate, citrate, bicarbonate, acetate, or glutamate may also be used. In general, a pH between about 5.5 and 8.0, between about 6.0 and 7.8, or between about 7.0 and 7.5 is employed.

The examples of ablation techniques provided above are not intended to be limiting, and the invention encompasses the use of essentially any cell ablation. Of course it is to be understood that certain techniques will be preferred for particular tissues or organs, depending upon the properties of these tissues and organs. One of ordinary skill in the art will be able to select an appropriate ablation technique and to vary parameters such as transit time, flow rate, pressure, temperature and concentration in order to achieve a desired degree of ablation. Namely, in order to ablate the endothelial cells lining the lumen surface of the blood vessels without affecting the underlying cell layers.

In certain embodiments the perfused ablating solution is a hypertonic solution (e.g. 3M NaCl) or a hypotonic solution (e.g. water). Aqueous hypotonic or low ionic strength solutions facilitate cell lysis through osmotic effects. Such solutions may comprise deionized water or an aqueous hypotonic buffer (e.g., at a pH of approximately 5.5 to 8, preferably approximately 7 to 7.5). In certain embodiments, the tissue or organ are perfused with alternating hypertonic and hypotonic solutions.

The ablating substance may an antibody or an enzyme, for example a protease (e.g. trypsin, collagenase) or a nuclease.

The blood vessels of the organ or tissue may be perfused simultaneously or sequentially, with one or more substances and with washing solutions (e.g. a physiological solution such as phosphate buffered saline, commonly used culture media) in order to stop the reaction of the substance with the tissue and remove it from the blood vessels.

Washing and preservation solutions can be perfused in order to remove residual substance from the vasculature of the tissue or organ, prior to transplanting it into a recipient.

The perfusion of the organ or tissue with the substance solution or the washing solution can occur at any amount, concentration, speed, temperature, pressure and duration. Preferably the concentration of the substance is low. More preferably, the substance is perfused at ultra-low concentration. Non-limiting examples 0.05% CHAPS or 0.05% SDS in calcium-free PBS at 4° C.

Preferably, the variable parameters of the perfusion (such as speed, duration, concentration and pressure), are adjusted or calibrated to achieve minimal exposure of the organ or tissue to the substance, but yet to result in ablation of the cells lining the luminal surface of the blood vessels. Such adjustment or calibration may be performed specifically for each tissue or organ intended for transplantation. The effect of the tested speed, duration, pressure and concentration can be easily determined as described in the examples below. For example, by preparing tissue sections of the treated organ or tissue and staining the tissue sections with appropriate antibodies capable of recognizing the presence of endothelial cells, e.g. Anti von Willebrand Factor antibody (e.g. cat. No. ab6994, Abcam), or anti-Human CD34 antibody (e.g. Catalog No. AF7227, R&D Systems).

For example, organs can be perfused at any pressure, preferably ranging between 10-500 mmHg, and at any flow rate, preferably at physiological flow rate, ranging between 1-500 ml per minute per 100 gram of tissue.

Kidneys can be perfused at a flow rate of 1100 ml per minute (400 ml per minute per 100 gram of tissue). Hearts can be perfused at a flow rate of 250 ml per minute (70 ml per minute per 100 gram of tissue).

The tissue or organ may be perfused at either normothermic or hypothermic temperatures, preferably at hypothermic temperatures. For hypothermic flush, static storage and hypothermic perfusion, the perfusing solution preferably contains little or no oxygen and preferably includes antioxidants, such as 2-ascorbic acid tocopherol, or enzymatic antioxidants (e.g., catalase and superoxide dismutase (SOD)). Normothermic and/or hypothermic perfusion, and preferably hypothermic perfusion, can be performed in vivo as well as in vitro. Such perfusion arrests ischemic injury in preparation for transport, storage and/or transplant of the organ.

One of ordinary skill in the art can select appropriate perfusion conditions without undue experimentation in view of the guidance set forth herein.

The blood vessels of the organ or tissue may be perfused in any direction, i.e. in a retrograde or antegrade fashion or in a combination of both fashions either sequentially or simultaneous, or in an alternate manner. In one embodiment, (in order to achieve sufficient homogeneous distribution of the substance at the microvascular level) the substance is perfused antegradely until it reaches capillaries, at half way of the blood-vessel circuit. Then, a washing solution is perfused retrogradely. Then, the substance is perfused retrogradely until it reaches the capillaries at half way of the blood-vessel circuit, followed by antegrade washing perfusion.

When positive pressure is applied antegradely to the arterial cannula, perfusion occurs through the capillary bed to the veins. When positive pressure is applied retrogradely to the venous cannula, perfusion occurs through the capillary bed to the arteries.

As used herein the term "transit time" or "physiological transit time" refers to the time interval that takes the blood to pass through a tissue or organ, from the input artery to the output vein. At a physiological flow rate, the intravascular transit time for most tissues and organs is in the order of a few seconds. Following are several examples of typical transit times for various organs:

Hepatic artery to vein transit time, and portal vein to hepatic vein transit time are in the order of 10 seconds (See for example Zhang H, et al Ultrasound Med. 2010 May; 29(5): 719-26).

Renal artery to vein transit time is in the order of 5 seconds, and may vary between 3-20 seconds (See for example, Clinical Nuclear Medicine, 4th edition, 2007, edited by Gary J. R. Cook, Michael N. Maisey, Keith E. Britton, and Vaseem Chengazi).

Whole lung pulmonary transit time, also called cardiopulmonary transit time is in the range of 2-3 seconds. (See for example Zavorsky G S, et al Exp Physiol. 2003 March; 88(2): 191-200).

Coronary transit time is in the range of 1 second (See for example Neishi Y, et al Proc Natl Acad Sci USA. 2005 Aug. 9; 102(32):11456-61. Epub 2005 Jul. 28).

The exact intravascular transit time of a tissue or organ can be tested ex-vivo, for example by using the following method: after the tissue or organ is prepared for pre-transplantation treatment, cannulated and perfused with preservation solution, a second preservation solution containing a non-toxic dye, such as phenol red, is perfused through the input artery until it is visualized in the output vein. The time interval is recorded and defined as the intravascular transit time.

Transit time perfusion protocol enables the control and fine selection of the type of cells or cell layers that will be ablated according to the method of the present invention. The transit time perfusion protocol is designed to allow minimal exposure of the cells or cell layers to the ablating substance which is present in the perfusion solution. Minimal exposure time can be achieved by adjusting the flow rate and duration of the perfusion to correlate with the physiological transit time of the tissue or organ.

Therefore, in one embodiment the duration of the perfusion is similar to the physiological transit time of the organ.

In order to achieve selective ablation of more cells or cell layers of the blood vessels or the tissue or organ, more than one cycle of transit time perfusion can be utilized.

In certain embodiments, subsequent to perfusion of the organ or tissue with the substance solution or with the washing solution, the tissue or organ intended for transplantation are further perfused with a protective solution, designed to protect the ablated blood vessels from undesired injuries (related for example to inflammation, proteolysis, oxidation, infection, thrombosis).

The protective solution can include one or more amino acids, one or more buffers and one or more inorganic salts.

The one or more amino acids can include L-glutamine, L-arginine, and the like. The one or more buffers can include phosphate buffered saline ("PBS"). The one or more inorganic salts can include sodium, calcium, potassium, and the like. The one or more substrates for metabolism can include glucose and other carbohydrates, lactate, fatty acids, other energy sources, vitamins, and the like.

The protective solution can also include a serum (see Liqiong Gui et al, 16(2) Tissue Engineering 173-84 (2010)). Suitable serums include human serum and non-human serums such as fetal bovine serum (FBS), porcine serum, and the like. Serums can be selected from the same or different species as the tissue or organ to be pre-treated and can even be provided from the donor of the organ and/or recipient of the pre-treated organ or tissue.

One or more serums can be mixed with other materials and can be administered as part of a single protective solution or as part of a follow-on protective solution.

In one embodiment, one or more compounds can be applied to the protective solution, for example, to preserve the treated tissue or organ, or to prepare the treated tissue or organ for cell re-population and/or to assist or stimulate cells during the re-population process. Such compounds include, but are not limited to, one or more growth factors (e.g., VEGF, DKK-I, FGF, BMP-I, BMP-4, SDF-I, IGF, and HGF), immune modulating agents (e.g., cytokines, glucocorticoids, IL2R antagonist, leucotriene antagonists), and/or factors that modify the coagulation cascade (e.g., aspirin, heparin-binding proteins, and heparin). In addition, the pre-treated organ or tissue can be further treated with, for example, irradiation (e.g., UV, gamma) to reduce or eliminate the presence of any type of microorganism remaining on or in the pre-treated organ or tissue.

In certain embodiments components of the protective solution can be included in the ablating substance solution. In other embodiments, the ablating substance solution and the protective solution can be administered simultaneously.

In certain embodiments the perfused substance is in a gas form, a liquid form or a semi-liquid, gel-like form.

The tissue or organ perfusion may be performed using organ perfusion devices known in the art, e.g. as disclosed in WO2005099588, WO2007124044, WO2007025215 or WO2011002926.

Figure 4:
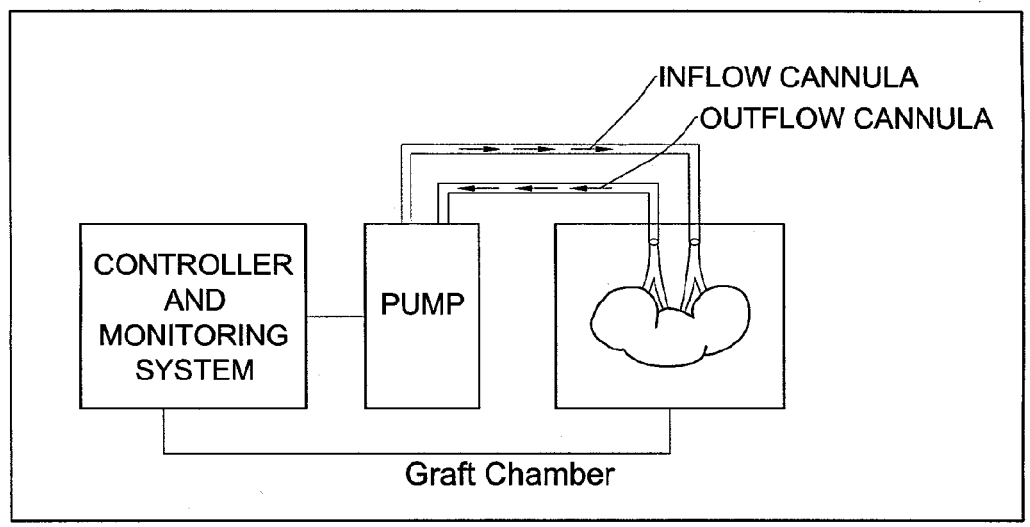
FIG. 4 is a schematic diagram of the apparatus of the invention.

FIG. 4 demonstrates a schematic representation of a perfusion apparatus suitable for use in the methods of the present invention.

In general, the organ is received within a perfusion chamber. The perfusion chamber can be any vessel capable of holding an organ or tissue and a preservation solution. In some embodiments, the perfusion chamber is a vessel such as a glass or plastic bowl, or an organ encasement.

At least one circuit circulates a solution (e.g. a preservation solution, a solution comprising the active substance, a washing solution or a protective solution) through the organ or tissue in the perfusion chamber. The circuit may include one or more pumps to promote the circulation of the perfusing solutions. The circuit can also include an oxygenator, a bubble trap, a heat exchanger, a pressure sensor, and one or more sampling ports.

The conditions of the ablation process may be monitored, automated and controlled by a control system to achieve highly selective ablation results. In one embodiment, the control system is associated with the organ perfusion device. The control system may be operated and controlled manually or automatically. The control system monitors the perfusion parameters e.g. pressure, flow rate, temperature, oxygen levels, electrolyte levels, and the like.

In certain embodiments the organ/tissue is subjected to the ablation treatment immediately after harvesting from the donor. In other embodiments the harvested organ or tissue are perfused with a preservation solution and maintained viable for varying periods of times prior to the ablation treatment.

In a specific embodiment, the present invention provides an ex vivo method of treating a human organ or tissue prior to transplantation thereof into a recipient, comprising:
(a) providing a human organ or tissue intended for transplantation;
(b) cannulating said organ or tissue at one or more vessels, thereby producing a cannulated organ; and
(c) perfusing the vasculature of said cannulated organ with an ablating substance solution comprising at least one substance capable of ablating the cells composing the blood vessels of said organ or tissue, via said one or more cannulations;
thereby obtaining a treated viable organ or tissue having reduced immunogenicity.

In another specific embodiment, the present invention provides a method of treating a non-human organ or tissue prior to transplantation thereof into a recipient, comprising:
(a) providing a non-human organ or tissue intended for transplantation;
(b) cannulating said organ or tissue at one or more vessels, thereby producing a cannulated organ; and
(c) perfusing the vasculature of said cannulated organ with an ablating substance solution comprising at least one substance capable of ablating the cells composing the blood vessels of said organ or tissue, via said one or more cannulations;
thereby obtaining a treated viable organ or tissue having reduced immunogenicity.

In a preferred embodiment said cells are the cells lining the lumenal surface of the blood vessels of said organ or tissue.

Repopulating the Ablated Blood Vessels with Cells

In one embodiment, the ablated blood vessels of the organ or tissue (the graft) may be re-seeded with cells, prior to transplantation of the organ/tissue into the recipient.

In accordance with the invention, the cells may be autologous, allogeneic or xenogeneic with respect to the host into which the graft is transplanted.

The cells of the invention can be obtained from any type of animal. In one embodiment, cells are isolated from a mammal. In a preferred embodiment the cells are human cells.

The cell may be any cell type, including, for example, a differentiated cell, a precursor cell, or a stem cell. Some non-limiting examples include an epithelial cell (including oral and gastrointestinal mucosal epithelia, urinary tract epithelia), endothelial cell, vascular endothelial cell, neural cell, epidermal cell, keratinocyte, melanocyte, osteoblast, intervertebral disc cell, chondrocyte, hepatocyte, pancreatic cell, hematopoietic cell, angioblast, B-cell, T-cell, erythrocyte, macrophage, monocyte, bone marrow mesenchymal cell, fibroblast, myoblast, muscle cell, cardiomyocyte, amniotic or placental cell, or stem cell. The invention also contemplates use of genetically engineered cells.

The seeded cells may be for example smooth muscle cells or endothelial cells. Preferably, the cells are endothelial cells. Preferably, the cells are autologous cells obtained from the recipient. Most preferably, the cells are autologous endothelial cells. Endothelial cells can be isolated using methods well known in the art for example as disclosed in McAllister, et al., Lancet 373, 1440-1446 (2009); and Deutsch, et al., J Vasc Surg 49, 352-362 (2009). Autologous endothelial cells can also be rapidly isolated from adipose tissue (Arts, et al., Lab Invest 81, 1461-1465 (2001)) or circulating blood (Kalka, et al., Proc Nat Acad Sci 97, 3422-3427 (2000); Hill, et al., New Eng J Med 348, 593-600 (2003).

The cell may be a stem cell. Types of stem cells include: undifferentiated stem cells, pluripotent stem cells, induced pluripotent stem cells or iPS cells, lineage-restricted stem cells, precursor cells, somatic stem cells, terminally differentiated somatic stem cells, cells expressing one or more markers of multilineage differentiation potential, cells expressing one or more markers of pluripotent stem cells, hematopoietic, neural, mesenchymal, postpartum, pancreatic, hepatic, retinal epithelial, olfactory bulb, endothelial, muscle, adipose-derived, ileac crest, bone marrow, periodontal ligament, oval and dermal stem cells and organ specific stem cells or progenitor cells, as well as embryonic stem cells.

In some cases the one or more pluripotent stem cell markers include one or more of OCT4, SOX2, UTF1, REX1, OXT2, NANOG, UTF1 AC133, CD9, DNMT3B, FOXD3, ALP, TERT, TERF, FZD9, GCNF, and SCGF.

In some cases the one or more markers are selected from a group consisting of a marker of adipogenic potential, osteogenic potential, neurogenic potential, chondrogenic potential, myogenic potential, and endothelial potential.

Exemplary adipogenic markers include AP0A2, APOD, APOE1 APOC1, and PPARG2. Exemplary osteogenic markers include BMP1, BMP2, OGN, and CTSK. Exemplary neurogenic markers include NTS, NRG1, MBP, MOBP, NCAM1, and CD56. Exemplary chondrogenic markers include COL4, COL5, COL8, CSPG2, and AGC1. Exemplary myogenic markers include MYF5, TMP1, MYH 11. Exemplary endothelial markers include VWF and NOS.

In some cases wherein cells are stem cells said cells may express more than one marker which may be one or more of the following: Oct3/4, Sox2, SSEA-1 (−), SSEA-3 (+), SSEA-4 (+), TRA-1-60 (+), TRA-1-81 (+), lacZ and GFP. The stem cells may be human or non human cells and may possess telomerase activity and a chromosomal methylation pattern characteristic of pluripotential cells.

The cells as used herein may also be immunologically inert cells, such as embryonic or fetal cells, stem cells, and genetically engineered cells.

In one embodiment, the cells are seeded onto the treated graft immediately upon their isolation.

In another embodiment the cells are expanded in culture for a defined period of time, prior to their seeding onto the treated graft. The time period may be for example, 1-5 population doublings, 5-10 doublings, 10-20 doublings, 20-50 doublings, 50-100 doublings, or more than 100 doublings; alternatively, the period of time in culture may be defined as from 30 minutes to 1 hour, from 1 to 6 hours, from 6-12 hours, from 12-24 hours, from 1-7 days, from 7-30 days, or from 1-6 months and more.

The optimal plating and culture conditions for a given animal cell type can easily be determined by one of ordinary skill in the art using only routine experimentation.

In some cases genetically engineered cells are used, wherein at least one cell of the population of cells is transfected with an exogenous polynucleotide encoding a diagnostic or a therapeutic product which can assist in tissue healing, replacement, maintenance and diagnosis. Some non-limiting examples of such products include—cytokines, growth factors, chemokines, chemotactic peptides, tissue inhibitors of metalloproteinases, hormones, angiogenesis modulators either stimulatory or inhibitory, immune modulatory proteins, neuroprotective and neuroregenerative proteins and apoptosis inhibitors. Some specific exemplary proteins include erythropoietin (EPO), EGF, VEGF, FGF, PDGF, IGF, IFN-α, IFN-β, TGF-α, TGF-β, TNF-α, IL-1, BDNF, GDF-5, BMP-7 and IL-6. The desired gene product can be either constantly or transiently expressed.

In one embodiment, the cells are treated with one or more differentiation agents.

In another embodiment, the cells are treated with one or more epigenetic altering agents.

Cell Culture Conditions

Prior to their seeding the cells are typically cultivated in a cell incubator at about 37° C. The incubator atmosphere is humidified and contains about 3-10% carbon dioxide in air. Culture medium pH is in the range of about 7.1-7.6, about 7.1-7.4, or about 7.1-7.3. Cells in closed or batch culture typically undergo complete medium exchange (i.e., replacing spent media with fresh media) every few days as required by the specific cell type, typically about every 2-3 days. Cells in perfusion culture (e.g., in bioreactors or fermentors) receive fresh media on a continuously recirculating basis.

Culture and differentiation agents useful in this invention include, by way of example, the following: medium refers to culture media for cells, as for example DMEM/F12 (Dulbecco's modified Eaglee's medium/Ham's F12, 1:1, Invitrogen, Carlsbad, Calif.), also encompassing possible alternatives, variations and improvements equivalent to this cell culture medium. In accordance with the particular needs of the cultured cell, the medium may be supplemented with serum preferably at least 5% serum, and more preferably about 15% serum. According to a particular embodiment of the invention, said serum is from bovine origin, more particularly bovine fetal serum, although synthetic and non-synthetic serums, from human and other animals may also be employed, as well as other synthetic or natural reagents, including mixtures thereof, that allow the culture of the cells.

In some cases the medium is serum free medium. In some other cases the cell culture medium may contain antibiotics such as penicillin and streptomycin and/or amino acids such as glutamine and other non-essential amino acids and mixtures thereof. The cells as described herein may be cultured in the presence of a single agent or multiple agents, concurrently or sequentially, for a variable duration of time.

The choice of a specific medium depends on the type of cultured cell and is well within the knowledge of a person skilled in the art.

This medium according to the present invention may comprise a) base medium, b) supplements, and c) growth factors. The base medium may include commonly used formulations well known to those skilled in the art including: RPMI, other commonly used basal media and preferably MEM or more preferably the alpha modification of MEM (α-MEM). These base medium also contain commonly used buffers to maintain physiological pH during the cell culture process, including but not limited to, sodium bicarbonate, HEPES and other buffer substances with a pKa in the physiological pH range. Supplements added to the base medium also include those commonly used in cell culture including transferrin or other iron-chelating agents, insulin (including natural or recombinant forms, insulin-like growth factors I & II, and related substances), trace elements, sodium pyruvate, non-essential amino acids, dextran at various molecular sizes, hydrocortisone, ethanolamine, glucose and the tri-peptide, glycyl-histidine-lysine. The appropriate concentrations & compositions for such supplements will be readily apparent to those skilled in the art. Optimal levels of cell culture medium constituents are often determined through an empirical process of testing potential concentrations against a defined endpoint including for example, the growth rate of the cells, etc. The exact formulation of various basal medium supplements may be varied from the list of specific supplements described above while still retaining the specific characteristics of the present invention that primarily includes the ability to support growth of the mesenchymal cell culture. The concentrations and other ingredients in a formulation of standard cell culture medium are well known to those of ordinary skill in the art.

The present invention also contemplates the use of "defined culture media" or "serum-free media" (SFM). A number of SFM formulations are commercially available, such as those designed to support the culture of endothelial cells, keratinocytes, monocytes/macrophages, fibroblasts, chondrocytes, or hepatocytes, which are available from GIBCO/LTI (Gaithersburg, Md.). For example, SFM formulations supporting in vitro culture of keratinocytes have been reported (e.g. U.S. Pat. Nos. 4,673,649 and 4,940,666).

The culture media of the present invention are typically sterilized to prevent unwanted contamination.

The media compositions and formulations of the invention include components which are known to the skilled artisan or can be otherwise deduced using routine methods.

In another embodiment of the invention the cultured cells may be reinforced with exogenously added extracellular matrix proteins, e.g., collagen, laminin, fibronectin, vitronectin, tenascin, integrin, glycosaminoglycan (hyaluronic acid, chondroitin sulfate, dermatan sulfate, heparan sulfate, heparin, keratan sulfate and the like), elastin and fibrin. In some embodiments of the invention growth factors and/or cytokines, such as vascular endothelial cell growth factors, platelet derived growth factors, epidermal growth factors, fibroblast growth factors, hepatocyte growth factors, insulin-like growth factors, and transforming growth factors are exogenously added to the culture.

The cells may be cultured on a surface of glass, ceramic or a surface-treated synthetic polymer. For example, polystyrene that has been subjected to a surface treatment, like γ-ray irradiation or silicon coating, may be used as a surface for cell culture.

Cells which grow to over 85% confluence form cell sheet layer that may be separated from the surface either mechanically, or by using proteolysis enzymes, such as trypsin or dispase. Non-enzymatic cell dissociation could also be used. A non-limiting example includes a mixture of chelators sold under the tradename CELLSTRIPPER (Mediatech, Inc., Herndon, Va.), a non-enzymatic cell dissociation solution designed to gently dislodge adherent cells in culture while reducing the risk of damage associated with enzymatic treatments.

In another embodiment, cells are cultured on a non-adherent surface at sufficient densities. This provides a cell sheet layer that has only a few structural defects as they are recovered with intracellular desmosome structures and the cell-to-cell connectivity and orientation is being kept intact.

In another embodiment, cells are cultured on thermoresponsive dishes supplied for example, by CellSeed, Inc. (Tokyo, Japan).

In this embodiment, the culture surface can be inherently non-adherent or can be rendered non-adherent by surface coatings well known to those skilled in the art. Commercially available cell growth support devices include, for example, the range of Corning® Ultra Low Attachment surface cell culturing products (Corning Inc., Corning N.Y.). These products have a hydrogel layer that is hydrophilic and neutrally charged covalently bound to polystyrene surfaces. Since proteins and other biomolecules passively adsorb to polystyrene surfaces through either hydrophobic or ionic interactions, this hydrogel surface naturally inhibits nonspecific immobilization via these forces, thus inhibiting subsequent cell attachment. Other biocompatible non-adherent materials include ePTFE, polystyrene, stainless steel, and some cross-linked cellulose derivatives. Examples thereof include cross-linked hydroxyalkyl celluloses e.g. hydroxyethyl cellulose, hydroxypropyl cellulose, methyl, thyl and methyl thyl celluloses. Cross-linked carboxyalkyl celluloses also included are carboxymethyl cellulose cross-linked with ethylene glycol diglycidyl ether (EGDGE) or 1,4 butanediol diglycidyl ether. Other materials include polyvinyl alcohol, poly (2-hydroxyethyl methacrylate) (Cellform® (MP Biomedicals, Irvine, Calif.), agarose, and crosslinked agarose.

Cells can also be seeded into or onto a natural or synthetic three-dimensional support matrix such as a preformed collagen gel or a synthetic biopolymeric material. Use of attachment factors or a support matrix with the medium of the present invention will enhance cultivation of many attachment-dependent cells in the absence of serum supplementation.

The cell seeding densities for each experimental condition can be selected for the specific culture conditions being used. For routine culture in plastic culture vessels, an initial seeding density of, for example, $1-5 \times 10^4$ cells per cm$^2$ is useful. In certain cases, micromass cultures are used.

Cell Transfection and Transformation of Cells in Culture

In accordance with the invention cells may be genetically altered by the introduction of a heterologous nucleic acid (e.g. DNA), using various methods known in the art including calcium-phosphate- or DEAE-dextran-mediated transfection, protoplast fusion, electroporation, liposome mediated transfection, direct microinjection and adenoviral or retroviral infection.

In a specific embodiment, a calcium-phosphate precipitate containing DNA encoding the gene(s) of interest can be prepared using the technique of Wigler et al. ((1979) Proc. Natl. Acad. Sci. USA 76:1373-1376). Cultures of adult stem cells (e.g., liver stem cells or adipose stem cells) or their progeny are established in tissue culture dishes. Twenty-four hours after plating the cells, the calcium phosphate precipitate containing approximately 20 µg/ml of the heterologous DNA is added. The cells are incubated at room temperature for 20 minutes. Tissue culture medium containing 30 µM chloroquine is added and the cells are incubated overnight at 37° C. Following transfection, the cells are analyzed for the uptake and expression of the foreign DNA. The cells may be subjected to selection conditions that select for cells that have taken up and expressed a selectable marker gene.

Selectable marker genes include, but are not limited to GFP (green fluorescence protein) or a drug resistance gene. Some non-limiting examples of drug-resistance genes for use in the invention include hygromycin resistance gene, neomycin resistant gene, ampicillin resistance gene, *E. coli* gpt gene or the like.

In another specific embodiment, the heterologous DNA is introduced into a multipotent stem cell using the technique of retroviral transfection. Various processes are known in the art for transferring retroviral vectors into cultured cells. For example, recombinant retroviruses harboring the gene(s) of interest are produced in packaging cell lines to produce culture supernatants having a high titer of virus particles (for example, $10^5$-$10^6$ pfu/ml). The recombinant viral particles are used to infect cultures of the stem cells (e.g., adult liver stem cells or adult adipose stem cells) or their progeny by, for example, incubating the cell cultures with medium containing the viral particles and 8 µg/ml polybrene for three hours. Following retroviral infection, the cells are rinsed and cultured in standard medium. The infected cells are then analyzed for the uptake and expression of the heterologous DNA. The cells can be subjected to selective conditions that select for cells that have taken up and expressed a selectable marker gene. Since the gene transferred by the retroviral vector is integrated into chromosomal DNA of the host stem cell, the gene is transmitted to the daughter cell and therefore can be expressed stably over long period.

In certain embodiments the cells described herein, such as adult stem cells (e.g., liver stem cells or mesenchymal stem cells such as adipocyte stem cells), and/or derivatives thereof (e.g., hepatocytes, adipocytes, osteocytes, myoblasts, or chrondrocytes) are immortalized by transformation with an immortalizing gene or construct. Some non-limiting examples of useful immortalizing genes include myc, ras, SV40 T antigen, Ewing's sarcoma oncogene, hTERT, dominant-negative p53, dominant-negative Rb (retinoblastoma), adenovirus EIa, adenovirus EIb, papilloma virus E6, papilloma virus E7, bcr-abl, neu, ret and other immortalizing genes such as Notch.

The cells of the invention can be immortalized by transfection or transduction with a suitable vector, homologous recombination, or other appropriate techniques, so that they express an immortalizing activity (e.g., the telomerase catalytic component (TERT)).

In certain embodiments the immortalizing gene used in accordance with the present invention, or a selection gene, can be inserted between a pair of site-specific recombination sequences so that the gene can be excised when desired. Representative site-specific recombinant sequences include the LoxP sequence, the FRT sequence, or the like. The LoxP sequence is used for performing homologous recombination by the enzyme Cre recombinase.

Cell Differentiation and Characterization
Differentiation

In certain embodiments, the present invention encompasses the seeding of stem cells that were induced to differentiate into specific cell types, such as epithelial cells, stromal cells, cardiac cells, bone cells and more. As is readily apparent to those skilled in the art, there are several methods known and under current development for the differentiation of stem/progenitor cell lines into differentiated target cell types. The present invention is not to be limited by the specific methods used to induce differentiation, but rather includes use of all such methods that are operationally defined as yielding the desired differentiation into a fully differentiated cell type.

For example, U.S. Pat. No. 6,596,274, and U.S. Pat. No. 5,811,094 disclose methods for cell differentiation.

Mesenchymal stem cells can be induced to differentiate into adipocytes, osteocytes, chondrocytes, myocytes, or neuronal cells (e.g., Blanat-Benard et al. (2004) Circ. Res. 94:223). Markers for mesenchymal stem cells and their differentiated cell types are known in the art, for example see Silva et al. (2003) Stem Cells 21:661.

In one specific embodiment, induction of differentiation includes incubating mesenchymal stem cells with a composition comprising IBMX, dexamethasone, indomethasone, and insulin, such that the cell differentiates into an adipocyte. Specifically, Adipocyte induction can be accomplished by culturing mesenchymal stem cells in a medium containing modified MEM with 10% FBS and supplemented with IBMX (I) (500 µM), dexamethasone (D) (1 µM), indomethacin (I) (1 µM), and insulin (I) (10 mg/ml) for three cycles of [IDI-1-2 days, insulin-1 day], and repeating the cycle three times. Successful induction of adipocytes can be determined using, e.g., Oil Red 0 staining of lipid vacuoles.

In yet another embodiment, the differentiation composition includes dexamethasone, L-ascorbate-2-phosphate, and β-glycerophosphate, such that the cell differentiates into an osteocyte. Specifically, induction of osteocyte differentiation is achieved by culturing stem cells in a medium composed of modified MEM with 10% FBS and supplemented with dexamethasone (0.1 µM), L-ascorbate-2-phosphate (50 µM), and β-glycerophosphate (10 mM) for about four weeks. Osteocytes can be identified by the presence of calcified extracellular matrix (ECM) using Von Kossa staining.

In yet another embodiment, the differentiation composition includes TGF-β1, L-ascorbate-2-phosphate, and insulin, such that the cell differentiates into a chondrocyte. Specifically, chondrogenic differentiation can be achieved by culturing mesenchymal stem cells in micromass culture using a medium composed of modified MEM containing 10% FBS and supplemented with TGF-β1 (10 ng/ml), L-ascorbate-2-phosphate (50 µM), and insulin (6.25 µg/ml). Cells with characteristics of chondrocytes generally develop in about one week and can be identified, e.g., using Alcian blue (pH 1.0) staining, which detects the presence of proteoglycans.

Myogenic differentiation can be induced, e.g., by culturing mesenchymal stem cells in modified MEM containing 5% horse serum and supplemented with 50 µM hydrocortisone for four to six weeks. Differentiated cells can be identified, e.g., by immunostaining with an antibody that specifically recognizes skeletal myosin.

The methods of inducing differentiation that are described herein are exemplary and are not intended to be limiting. Other suitable methods of identifying specific differentiated cell types are known in the art and can be used to identify differentiated cells obtained from adult stem cells cultured using the methods described herein.

Characterization

The process of making a differentiated cell from a stem cell is accompanied by changes in the expression of cell markers. There are also unique pluripotent stem cells markers as well as markers of multilineage differentiation. Such cell markers are typically expressed as mRNA and/or protein. Detection of the mRNA or protein markers may be performed by any method known in the art. In some embodiments, nucleic acids and/or proteins will be isolated from the cells and then analyzed.

Tissue-specific protein markers can be detected using any suitable immunological technique such as flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium.

The expression of tissue-specific markers can also be detected at the mRNA level by Northern blot analysis, dot-blot hybridization analysis, or by reverse transcriptase initiated polymerase chain reaction (RT-PCR) using sequence-specific primers in standard amplification methods. See for example, U.S. Pat. No. 5,843,780. Sequence data for the particular markers can be obtained from public databases such as GenBank (URL www.ncbi.nlm.nih.gov:80/entrez). Expression of tissue-specific markers as detected at the protein or mRNA level is considered positive if the level is at least 2-fold, and, in certain instances, more than 10- or 50-fold above that of a control cell, such as an undifferentiated adult liver stem cell, a fibroblast, or other unrelated cell type.

In one embodiment, the repopulation of the blood vessels is performed by perfusing the treated organ or tissue with a solution containing the recipient's cells which thereby replace the ablated cells.

After seeding and re-popluating, the cells on the treated tissue or organ are optionally subjected to an expansion medium or to a differentiation medium or cultured in the presence of tissue-specific growth factors. The seeded tissue or organ is then transplanted into a subject in need thereof. The transplanted tissue or organ may support additional cell growth in vivo.

The number of cells that is used to re-populate the pre-treated tissue or organ is dependent on both the organ (e.g., which organ, the size and weight of the organ) or tissue and the type and developmental stage of the re-populating cells. Different types of cells may have different tendencies as to the population density those cells will reach. Similarly, different organs or tissues may be re-populated at different densities. By way of example, a treated organ or tissue (whose endogenous cells were ablated as described above) can be seeded with at least about 1,000 re-populating cells, e.g., at least 10,000, 100,000, 1,000,000, 10,000,000, or 100,000,000 repopulating cells; or can have from about 1,000 cells/mg tissue (wet weight, i.e., prior to treatment) to about 10,000,000 cells/mg tissue (wet weight) attached thereto.

Cells can be introduced to the treated organ or tissue by injection into one or more locations. In addition, more than one type of cell (i.e., a cocktail of cells) can be introduced into the treated organ or tissue. For example, a cocktail of cells can be injected at multiple positions in the treated organ or tissue or different cell types can be injected into different portions of the treated organ or tissue. Alternatively, or in addition to injection, re-populating cells or a cocktail of cells can be introduced by perfusion into a cannulated vessel containing the treated organ or tissue. For example, cells can be perfused into the treated organ using a perfusion medium, which can then be changed to an expansion and/or differentiation medium to induce growth and/or differentiation of the re-populating cells. During re-population, an organ or tissue is maintained under conditions in which at least some of the re-populating cells can multiply and/or differentiate within and on the treated organ or tissue. Those conditions include, without limitation, the appropriate temperature and/or pressure, electrical and/or mechanical activity, force, the appropriate amounts of $O_2$ and/or $CO_2$, an appropriate amount of humidity, and sterile or near-sterile conditions. During re-population, the treated organ or tissue and the cells attached thereto are maintained in a suitable environment. For example, the cells may require a nutritional supplement (e.g., nutrients and/or a carbon source such as glucose), exogenous hormones or growth factors, and/or a particular pH.

The seeded cells can be allogeneic to the pre-treated organ or tissue (e.g., a human treated organ or tissue seeded with human cells), or can be xenogeneic to the treated organ or tissue (e.g., a pig treated organ or tissue seeded with human cells).

In some instances, the treated organ or tissue generated by the methods described herein is to be transplanted into a patient. In those cases, the cells used to re-populate the treated organ or tissue can be obtained from the patient (the recipient) such that the regenerative cells are autologous to the patient. Cells from a patient can be obtained from, for example, blood, bone marrow, tissues, or organs at different stages of life (e.g., prenatally, neonatally or perinatally, during adolescence, or as an adult) using methods known in the art. Alternatively, cells used to re-populate the treated organ or tissue can be syngeneic (i.e., from an identical twin) to the patient, cells can be human lymphocyte antigen (HLA)-matched cells from, for example, a relative of the patient or an HLA-matched individual unrelated to the patient, or cells can be allogeneic to the patient from, for example, a non-HLA-matched donor.

In certain instances, the treated organ or tissue is re-populate with cells in vivo (e.g., after the organ or tissue has been transplanted into an individual). In vivo re-population may be performed as described above (e.g., by injection) with, for example, any of the cells described herein. Alternatively or additionally, in vivo seeding of the pre-treated organ or tissue with endogenous cells may occur naturally or be mediated by factors delivered to the re-populated tissue.

In one embodiment, an effective amount of anticoagulants and/or antiaggregants is administered to the patient receiving the organ or tissue transplant of the invention, in order to reduce the thrombogenicity of the transplanted tissue or organ.

The transplanted tissue or organ can be allogenic, xenogenic, or bio-engineered.

In another aspect, the present invention provides a method of treating a patient in need of transplantation, comprising:

(a) obtaining a treated viable organ or tissue having reduced immunogenicity, wherein said organ or tissue are prepared in accordance with the methods of the invention; and
(b) transplanting said treated viable organ or tissue in the patient.

In accordance with the invention, a patient in need of transplantation may be any patient suffering from a disease or disorder that can be alleviated by transplanting a tissue or an organ. Examples of diseases, disorders, or conditions that may be treated using the treated viable organ or tissue of the invention include neurological, endocrine, structural, skeletal, vascular, urinary, digestive, integumentary, endocrine, kidney, bladder, cardiovascular, cancer, circulatory, digestive, hematopoeitic, and muscular diseases, disorders, and conditions.

In certain embodiments the viable treated organ or tissue of the present invention is used as as a bridge to transplantation, or after a transplantation failure.

The viable treated organ or tissue of the present invention may be transplanted orthotopically, namely at the original site of the organ or tissue, or heterotopically, namely at a different location.

Following transplantation of the viable treated organ or tissue of the present invention, the status of the immunological tolerance of the recipient subject to the graft is preferably closely monitored according to standard methods known in the art.

Various methods may be employed to assess the subject's immunological tolerance to the graft, or the transplant rejection (graft rejection).

For example, the tolerance may be assessed by monitoring subject-specific leukocyte or T-lymphocyte infiltration of the graft, and/or by monitoring the histological appearance of organ or tissue specific structures using methods well known in the art (for example, Dekel B. et al., 1999. hit Immunol 11, 1673; Dekel B. et al., 1997 Transplantation 64, 1541).

Infiltration of subject leukocytes, neutrophils, natural killer (NK) cells, or T-lymphocytes into the graft are typically indicative of suboptimal engraftment and graft rejection Ample guidance for ascertaining graft rejection is provided in the art (for example: Kirkpatrick C H. and Rowlands D T Jr., 1992 JAMA 268, 2952; Higgins R M. et al, 1996. Lancet 348, 1208; Suthanthiran M. and Strom T B. 1996. New Engl. J. Med. 331, 365; Midthun D E. et al, 1997. Mayo Clin Proc. 72, 175; Morrison V A. et al, 1994. Am J. Med. 97, 14; Hanto D W., 1995. Annu Rev Med. 46, 381; Senderowicz A M. et al, 1997. Ann Intern Med. 126, 882; Vincenti F. et al, 1998. New Engl. J. Med. 338, 161; Dantal J. et al. 1998. Lancet 351, 623).

According to a further aspect of the present invention there is provided a method of evaluating the suitability of a pre-treated organ or tissue for transplantation of a graft of the organ or tissue into a mammalian subject.

The method according to this aspect of the present invention is preferably effected by evaluating a test transplant taken from the organ or tissue for presentation of the immunogenic cells lining the luminal surface of blood vessels of the tissue or organ, such as the endothelial cells, capable of stimulating or enhancing an immune response in the subject prior to and/or following transplantation of the test transplant into a mammalian test recipient.

According to the teachings of the present invention, a test transplant found not presenting the immunogenic cells will be optimal for transplantation.

In general, the higher the level of ablation of the immunogenic cells lining the luminal surface of the blood vessels, the more suitable the organ or tissue graft will be for transplantation.

Surgical approaches and principles of transplant surgery are well known in the art, for example such procedures are described in: Transplantation Surgery (Hakim & Danovitch Eds., Springer 2010)

Transplanting the graft may be effected in numerous ways, depending on various parameters, such as, for example, the graft type; the type, stage or severity of the disorder; the physical or physiological parameters specific to the individual subject; and/or the desired therapeutic outcome. Optionally, when transplanting a graft of the present invention into a subject having a defective or diseased tissue or organ, it may be advantageous to first remove the defective or diseased tissue or organ from the subject so as to enable optimal development of the graft, and structural/functional integration thereof with the anatomy/physiology of the subject.

One of ordinary skill in the art, such as a physician, in particular a transplant surgeon specialized in the disorder, would possess the expertise required for applying the teachings of the present invention towards treating essentially any disorder in the subject amenable to tissue or organ transplantation.

Depending on the transplantation context, in order to facilitate engraftment of the graft, the method of the invention may further comprise treating the subject with a minimal immunosuppressive regimen prior to, concomitantly with, or following transplantation of the graft.

Various types of immunosuppressive regimens may be used to immunosuppress the subject. Examples of suitable types of immunoppressive regimens include administration of immunosuppressive drugs, tolerance inducing cell populations, and/or immunosuppressive irradiation.

Ample guidance for selecting and administering suitable immunosuppressive regimens for transplantation is provided in the literature of the art (for example, refer to: Kirkpatrick C H. and Rowlands D T Jr., 1992. JAMA. 268, 2952; Higgins R M. et al, 1996. Lancet 348, 1208; Suthanthiran M. and Strom T B., 1996. New Engl. J. Med. 331, 365; Midthun D E. et al, 1997. Mayo Clin Proc. 72, 175; Morrison V A. et al, 1994. Am J. Med. 97, 14; Hanto D W., 1995. Annu Rev Med. 46, 381; Senderowicz A M. et al, 1997. Ann Intern Med. 126, 882; Vincenti F. et al, 1998. New Engl. J. Med. 338, 161; Dantal J. et al 1998. Lancet 351, 623).

Preferably, the immunosuppressive regimen consists of administering at least one immunosuppressant drug to the subject.

Examples of suitable immunosuppressive drugs include, but are not limited to, CTLA4-Ig, anti-CD40 antibodies, anti-CD40 ligand antibodies, anti-B7 antibodies, anti-CD3 antibodies (for example, anti-human CD3 antibody OKT3), methotrexate (MTX), prednisone, methyl prednisolone, azathioprene, cyclosporin A (CsA), tacrolimus, cyclophosphamide and fludarabin, mycophenolate mofetil, daclizumab [a humanized (IgG1 Fc) anti-IL2R alpha chain (CD25) antibody], anti-T-lymphocyte antibodies conjugated to toxins (for example, cholera A chain, or *Pseudomonas* toxin), and an agent capable of inhibiting the activity of the protein mammalian-target-of-rapamycin (mTOR).

Examples of agents capable of inhibiting the activity of mTOR include rapamycin (sirolimus) and rapamycin analogs, such as CCI-779, RADOO1, and AP23573. Rapamycin binds to the immunophilin FK506-binding protein (FK506BP) 12, and this protein/drug complex binds to and inhibits the activity of mTOR, a protein involved in regulating the G1 to S phase transition.

Ample guidance for administering immunosuppressant drugs such as CTLA4-Ig so as to facilitate immunosuppression of a transplant recipient is provided in the literature of the art (for example, refer to: Benhamou P Y., 2002, Transplantation 73, S40; Najafian N, and Sayegh M H., 2000. Expert Opin Investig Drugs 9, 2147-57). Treatment of a recipient subject of the present invention with CTLA4-Ig is effected by administering CTLA4-Ig to the subject at a daily dose selected from a range of 1 to 100 milligrams per kilogram body weight, and most preferably about 20 milligrams per kilogram body weight.

For further elaboration of general techniques useful in the practice of this invention, the practitioner can refer to standard textbooks and reviews in cell and tissue culture, embryology, and molecular biology. General techniques in cell culture and media collection are outlined in Large Scale Mammalian Cell Culture (Hu et at., Curr. Opin. Biotechnol. 8:148, 1997); Serum-free Media (K. Kitano, Biotechnology 17:73, 1991); Large Scale Mammalian Cell Culture (Curr. Opin. Biotechnol. 2:375, 1991); and Suspension Culture of Mammalian Cells (Birch et al., Bioprocess Technol. 19:251, 1990). Textbooks on the subject include General Techniques in Cell Culture (Harrison & Rae, Cambridge, 1997); Animal Cell Culture Methods (Barnes & Mather, eds., Academic Press, 1998); Culture of Animal Cells (I. Freshney, 4th.ed., John Wiley & Sons, 2000); Guidebook to the Extracellular Matrix, Anchor, and Adhesion Proteins (Kreis & Vale, eds., Oxford, 1999); Handbook of Cellular Manufacturing Systems (S. A. Irani, ed., John Wiley & Sons, 1999). The properties, culture, and differentiation of embryonic stem cells are described in *Teratocarci nomas* and embryonic stem cells: A practical approach (EJ. Robertson, ed., IRL Press Ltd. 1987); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., al., 1993). Differentiation of stem cells is reviewed in Robertson, Meth. Cell Biol. 75:173, 1997; and Pedersen, Reprod. Fertil. Dev. 10:31, 1998. References that further describe the culturing of particular cell types are listed further on in the disclosure.

General biochemical techniques are described in Short Protocols in Molecular Biology (Ausubel et al., eds., 4th ed. 1999). Methods of protein chemistry are described generally in Protein Methods (Bollag et al., 1996); Guide to Protein Purification (Deutscher et al., eds., Methods Enzymol. vol. 182, Academic Press, 1997); Protein Analysis and 5 Purification (L M. Rosenberg, Springer Verlag, 1996).

EXAMPLES

Example 1

Preparation of a Tissue or Organ for Pre-Treatment

A heart-beating mammal donor is systemically heparinized in order to minimize the risk of thrombus formation. Heparanization is done by intravenous administration of 100-400 Units of heparin/Kg of body weight of the donor. Surgical removal of donor tissue or organ is done in a sterile working environment, such as an operating room. Connective tissue is removed from the tissue or organ and its adjacent blood vessels. The main artery and vein are ligated using nonabsorbable sutures or clamped using hemostatic clamps, at segments of the vessels that are far away from the vascular anastomoses performed in the recipient. Then the tissue or organ and its adjacent blood vessels are placed in a preservation solution e.g. a 4° C. sterile 0.9% saline solution, supplemented with 40 Units/ml of heparin, and kept at 4° C. until further processing.

In another example, the tissue or organ is obtained from a human donor under beating heart conditions.

Example 2

Cannulation and Perfusion of a Tissue or Organ

The free ends of the artery and vein of the tissue or organ are cannulated. Cannula diameter is chosen according to the size and type of the blood vessel. The cannula leads perfusion solutions into the artery or vein, and is connected directly to a perfusion set. A double line perfusion set is used to allow fast flow of two types of perfusion solutions alternatively. A drip chamber along the line allows easy viewing and control. Air filters prevent air bubbles to pass through the lines. The perfusion set is connected to an infusion pump. The pump allows control over the flow rate, pressure, volume, and perfusion time of the perfusion solution. The specific flow rate, pressure, volume, and perfusion time at a particular temperature varies depending on the particular tissue or organ being perfused.

After the tissue or organ is mounted on the apparatus of the invention (FIG. 4) and cannulated, antegrade perfusion is started with cold, heparinized 0.9% saline solution to reestablish constant flow. After 2-3 minutes of stable flow, the detergent-based ablation process is initiated as set forth herein.

Example 3

Selective Ablation of the Endothelial Cells Lining the Luminal Surface of Blood Vessels Once anterograde perfusion at a constant rate is established through one line of the double line perfusion set, a detergent-based solution is mounted on the apparatus of the invention and connected to the perfusion set. In order to achieve a highly selective ablation of the single cell layer of endothelial cells lining the luminal surface of the cannulated vessel, a non-denaturing detergent such as 3-[(3-Cholamidopropyl)dimethylammonio]-1-propanesulfonate (CHAPS) is used. A solution of 0.05% CHAPS in calcium-free PBS at 4° C. is perfused at a flow rate of 400 ml/min for 3 seconds through the second line of the double line perfusion set. Then the cannulated vessel is perfused with a preservation solution in order to wash away the detergent. Washing is done at a flow rate of 50 ml/min until it reaches the end of the cannulated vessel.

Example 4

Perfusion and Washing with a Third, Protective Solution

A third, protective solution is mounted on the apparatus of the invention and connected to the perfusion set. The protective solution contains a mixture of protease inhibitors in calcium-free PBS that protect the extracellular matrix proteins found at the sub-endothelial layers from being degraded by endogenous enzymes. Perfusion of the tissue or organ with the protective solution allows washing of residual cellular components, enzymes, or detergents.

Example 5

Transit Time Perfusion Protocol

Anterograde Transit Time Perfusion Protocol

The input artery of a tissue or organ is cannulated, and anterograde perfusion at a constant rate is established through one line of the double line perfusion set. An active solution of 0.05% CHAPS in calcium-free PBS at 4° C. is mounted on the apparatus of the invention and connected to the second line of the perfusion set. The active solution is perfused at a flow rate of 100 ml/min for a duration that correlates exactly to the calculated transit time. Then the perfusion with the active solution is stopped, and the cannulated artery is perfused with a preservation or washing solution at a flow rate of 50 ml/min for duration of 60 seconds in order to wash away the active solution.

Sequential Anterograde-retrograde Transit Time Perfusion

The input artery of a tissue or organ is cannulated, and anterograde perfusion at a constant rate is established through one line of the double line perfusion set. The output vein is cannulated too. An active solution of 0.05% CHAPS in calcium-free PBS at 4° C. is mounted on the apparatus of the invention and connected to the second line of the perfusion set. The active solution is perfused anterogradely through the cannulated artery at a flow rate of 100 ml/min for a duration that correlates exactly to half of the calculated transit time, until it reaches capillaries, at half way of the blood-vessel circuit. Then, a washing solution is perfused retrogradely through the cannulated vein at a flow rate of 50 ml/min for 60 seconds. Next, the active solution is perfused retrogradely through the cannulated vein at a flow rate of 100 ml/min for a duration that correlates exactly to half of the calculated transit time, until it reaches capillaries, at half way of the blood-vessel circuit. Then, a washing solution is perfused anterogradely through the cannulated artery at flow rate of 50 ml/min for 60 seconds.

In order to achieve selective ablation of more cells or cell layers of the blood vessels or the tissue or organ, one or more perfusion cycles can be utilized.

Example 6

In-Vitro Evaluation of a Treated Tissue or Organ

Histology

Tissue samples are fixed in 4% paraformaldehyde, gradually dehydrated in ethanol and embedded in paraffin. Sections were stained with Hematoxylin and Eosin (H&E) for general histomorphology. The following histological staining is performed following the manufacturer's instructions:

Masson's Trichrome Stain (Sigma) and Sirius Red (Gurr-BDH, UK) are used detection of extracellular matrix collagens, Movat Pentachrome stain (American Mastertech Scientific) is used for the detection of elastic fibers, collagens and mucins, Verhoeff's Stain (American Mastertech Scientific) is used for the detection of elastic fibers, Toluidine blue (Serva, Germany) and Alcian Blue (Dako) are used to detect proteoglycans and glycosaminoglycans.

Immunohistochemistry

For immunohistochemistry, paraffin-embedded tissue sections are stained with primary antibodies, diluted in primary antibody diluent (Dako). The following primary antibodies can be used: Anti von Willebrand Factor antibody (cat. No.

ab6994, Abcam), anti-Human CD34 antibody (Catalog No. AF7227, R&D Systems), anti-Fibrinogen antibody (Catalog No. AF1918, R&D Systems), anti-Collagen IV antibody (Catalog No. ab6586, Abcam), anti Laminin antibody (Catalog No. M063801, Dako), anti-Collagen I antibody (Catalog No. ab34710, Abcam), anti-HLA Class 1 ABC antibody (Catalog No. ab70328, Abcam), anti-HLA DR antibody (Catalog No. ab20181, Abcam). Suitable secondary antibodies are used for visualization. Slides are covered with a cover slip in mounting medium containing DAPI for nuclear counterstaining.

Scanning Electron Microscopy

Tissue samples are fixed with 3% glutaraldehyde in 0.1M sodium cacodylate buffer, followed by gradual dehydration in ethanol, and then dried using hexamethyldisilazane (Sigma). Samples are then sputter coated with gold and viewed under field-emission scanning electron microscope (Hitachi High Technologies).

Example 7

Re-Population with Cells

It may be desirable to facilitate re-population of the pre-treated tissue or organ with cells prior to transplantation into a recipient. The re-populating cells can replace the ablated cells lining the lumenal surface of the blood vessels of the tissue or organ intended for transplantation.

Re-population of the pre-treated tissue or organ is facilitated by adding cells which are non-immunogenic to the recipient, preferably autologous, prior to transplantation into the recipient. Alternatively, re-population may occur in vivo, post-transplantation.

The ability of treated blood vessel surfaces to be re-populated with cells is demonstrated in vitro by seeding human cells on the treated vessels.

Re-population is done by perfusing the tissue or organ with a cell culture solution comprising autologous cells, using a perfusion apparatus as described above.

Unattached cells are washed away.

The efficiency of the re-population procedure is evaluated by preparing tissue sections of the blood vessels and performing histological analysis or scanning electron microscopy analysis (SEM).

Example 8

In-Vivo Transplantation of a Pre-Treated Tissue or Organ

Preparation of the Tissue or Organ for Transplantation

The restoring of organ viability may be accomplished by restoring high energy nucleotide (e.g., adenosine triphosphate (ATP)) levels and enzyme levels in the organ, which were reduced by warm ischemia time and/or hypoxia, by perfusing the organ with an oxygenated medical fluid, such as an oxygenated cross-linked hemoglobin-based bicarbonate medical fluid, at normothermic or near-normothermic temperatures.

Kidney Transplantation Procedure

The transplantation experiments are performed on animals demonstrating normal renal function before the start of the surgery. All experiments were performed following the principles of laboratory animal care according to the NIH standards. Donor and recipient animals are purchased from different vendors to ensure that the donors and recipients are unrelated. Kidneys are nephrectomized, a cannula is placed in the renal artery, flushed to remove the blood, and then connected to the apparatus of the invention, such as described in Example 2. After pre-treatment and subsequent washing perfusion, the kidneys are reimplanted with nephrectomy of the contralateral kidney in the autotransplants and the two native kidneys in the allotransplants. Serum creatinine level and urine output are measured to assess transplant survival and functionality.

Liver Transplantation Procedure

The transplantation experiments are conducted in accordance to the principles of laboratory animal care according to the NIH standards. Miniature swine (24 to 32 kg) are used as donors. Standard liver procurement with in situ aortic flush with UW solution is performed. Donor livers are cannulized and connected to the apparatus of the invention, such as described in Example 2. After pre-treatment and subsequent washing perfusion, donor livers are transplanted orthotopically into swine (26 to 31 kg) without venovenous bypass using the method described by Oike (Oike et al., Transplantation, 71:328, 2001). Recipient swine received intravenous dextrose infusion for 48 hours post-transplant Animals also receive oral amoxicillin. Serum aspartate aminotrasferase and total bilirubin are measured to assess transplant survival and functionality.

The foregoing embodiments and advantages are merely exemplary and are not to be construed as limiting the present invention. The present teachings can be readily applied to other types of apparatuses. Also, the description of the embodiments of the present invention is intended to be illustrative and not to limit the scope of the claims. Many alternatives, modifications, and variations will be apparent to those skilled in the art.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of treating an organ or a tissue prior to transplantation thereof into a recipient, comprising:
    (a) providing an organ or a tissue intended for transplantation; and
    (b) ablating the cells composing the blood vessels of said organ or tissue while keeping the remaining cell layers in the organ or the tissue intact and viable, thereby obtaining a treated viable organ or tissue having reduced immunogenicity.

2. The method of claim 1, wherein step (b) comprises:
    (a) ablating the cells of the tunica intima cell layer lining the lumenal surface of the blood vessels of said organ or tissue; or
    (b) ablating the cells composing the tunica intima cell layer and the tunica media cell layer of the blood vessels of said organ or tissue; or
    (c) ablating the cells composing the tunica intima cell layer, the tunica media cell layer and the tunica adventitia cell layer of the blood vessels of said organ or tissue.

3. The method of claim 1, wherein said step of ablating the cells comprises subjecting said organ or transplant to at least one cycle of perfusion with an ablating substance solution comprising at least one substance capable of destroying or neutralizing said cells.

4. The method of claim 3, wherein said at least one substance is selected from a group consisting of a solubilizing agent, a detergent, a chelating agent, an enzyme, an antibody, a hypertonic solution, a hypotonic solution, a dehydrating agent, and any combination thereof.

5. The method of claim 3, wherein said perfusion is performed for a duration of about the transit time of said organ or tissue.

6. The method of claim 3, wherein said perfusion is performed for a duration which is smaller than the transit time of said organ or tissue.

7. The method of claim 6, wherein said perfusion is performed for a duration which is half the transit time of said organ or tissue.

8. The method of claim 3, wherein said perfusion is performed for a duration which is longer than the transit time of said organ or tissue.

9. The method of claim 3, wherein said perfusion is performed for a duration of about 1 second to about 5 minutes.

10. The method of claim 1, wherein the organ or the tissue are selected from the group consisting of a heart, lung, kidney, liver, pancreas, skin, uterus, bone, cartilage, small or large bowel, bladder, brain, breast, blood vessels, esophagus, fallopian tube, gallbladder, ovaries, pancreas, prostate, placenta, spinal cord, limb including upper and lower, spleen, stomach, testes, thymus, thyroid, trachea, ureter, urethra, uterus, vascular tissue, skin tissue, hepatic tissue, pancreatic tissue, neural tissue, urogenital tissue, gastrointestinal tissue, skeletal tissue including bone and cartilage, adipose tissue, connective tissue including tendons and ligaments, amniotic tissue, chorionic tissue, dura, pericardia, muscle tissue, glandular tissue, facial tissue and ophthalmic tissue.

11. The method of claim 3, further comprising perfusing said organ or transplant with a preservation solution prior to, and/or after subjecting the organ or transplant to the at least one cycle of perfusion with the ablating substance solution.

12. The method of claim 3, further comprising perfusing said organ or transplant with a protective solution during and/or after subjecting the organ or transplant to the at least one cycle of perfusion with the ablating substance solution.

13. The method of claim 3, further comprising perfusing said organ or transplant with a washing solution prior to, after and/or in between the perfusion cycles.

14. The method of claim 1, wherein the blood vessels of the organ or tissue are perfused in a retrograde fashion, in an antegrade fashion or in a combination of retrograde and antegrade fashions.

15. The method of claim 1, further comprising contacting said treated viable organ or tissue with a population of cells under conditions in which said cells engraft, multiply and/or differentiate on the lumenal surface of the blood vessels of the treated viable organ or tissue.

* * * * *